US012070468B2

(12) United States Patent
Shawber et al.

(10) Patent No.: US 12,070,468 B2
(45) Date of Patent: Aug. 27, 2024

(54) COMPOSITIONS AND METHODS FOR THE TREATMENT AND PREVENTION OF VASCULAR MALFORMATIONS

(71) Applicant: The Trustees of Columbia University in the City of New York, New York, NY (US)

(72) Inventors: Carrie J. Shawber, Washington, NJ (US); June K. Wu, New York, NY (US); Ajit Muley, San Mateo, CA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 17/984,734

(22) Filed: Nov. 10, 2022

(65) Prior Publication Data

US 2023/0141664 A1    May 11, 2023

Related U.S. Application Data

(63) Continuation of application No. PCT/US2021/032374, filed on May 14, 2021.

(60) Provisional application No. 63/024,670, filed on May 14, 2020.

(51) Int. Cl.
| | | |
|---|---|---|
| *A61K 31/145* | (2006.01) | |
| *A61K 31/407* | (2006.01) | |
| *A61K 31/501* | (2006.01) | |
| *A61K 31/69* | (2006.01) | |
| *A61K 38/06* | (2006.01) | |
| *A61K 38/07* | (2006.01) | |
| *A61P 9/14* | (2006.01) | |

(52) U.S. Cl.
CPC ............ *A61K 31/69* (2013.01); *A61K 31/145* (2013.01); *A61K 31/407* (2013.01); *A61K 31/501* (2013.01); *A61K 38/06* (2013.01); *A61K 38/07* (2013.01); *A61P 9/14* (2018.01)

(58) Field of Classification Search
CPC .... A61K 31/69; A61K 31/145; A61K 31/407; A61K 31/501; A61K 38/06; A61K 38/07; A61K 38/05
See application file for complete search history.

(56) References Cited

U.S. PATENT DOCUMENTS

| 6,288,110 B1 * | 9/2001 | Marikovsky ............ A61P 35/04 514/483 |
|---|---|---|
| 8,871,781 B2 | 10/2014 | At et al. |
| 10,537,587 B2 | 1/2020 | He |
| 2006/0141472 A1 | 6/2006 | Vikkula et al. |
| 2018/0117055 A1 | 5/2018 | Baselga et al. |
| 2018/0235994 A1 | 8/2018 | Comi et al. |
| 2020/0024666 A1 | 1/2020 | Greene et al. |
| 2020/0056238 A1 | 2/2020 | Hakonarson et al. |

FOREIGN PATENT DOCUMENTS

| WO | WO-2018045078 A2 * | 3/2018 | ......... A61K 31/4184 |
|---|---|---|---|
| WO | WO-2018126192 A1 * | 7/2018 | ......... A61K 31/4184 |
| WO | 2021050743 A1 | 3/2021 | |

OTHER PUBLICATIONS di Blasio et al. "PI3K/mTOR inhibition promotes the regression of experimental vascular malformations driven by PIK3CA-activating mutations", Cell Death and Disease, 2018, 15 pages (Year: 2018).*
Lukey et al. "A randomised, placebo-controlled study of omipalisib (PI3K/mTOR) in idiopathic pulmonary fibrosis", Eur Respir J, 2019, 12 pages (Year: 2019).*
Velcade, "How VELCADE is given", Apr. 25, 2020, https://www.velcade.com/about-velcade/how-velcade-is-given/). (Year: 2020).*
Ribatti et al. "New Insights in Anti-Angiogenesis in Multiple Myeloma", International Journal of Molecular Sciences, 2018, 14 pages (Year: 2018).*
U.S. National Library of Medicine, "Carfilzomib Injection", MedlinePlus, https://medlineplus.gov/druginfo/meds/a612031.html, 2017, pages (Year: 2017).*
Cox et al. "Vascular Malformations: A Review", Seminars in Plastic Surgery, 2014, pp. 58-63 (Year: 2014).*
Riss et al. "Cell Viability Assays". 2016. Assay Guidance Manual [Internet]. Bethesda (MD): Eli Lilly & Company and the National Center for Advancing Translational Sciences; 2004—. Available from: https://www.ncbi.nlm.nih.gov/books/NBK144065/). (Year: 2016).*
Green and Gross "Vascular Anomalies: From a Clinicohistologic to a Genetic Framework", Plastic and Reconstructive Surgery • May 2018, 709e-717e (Year: 2018).*
Basler et al., Co-inhibition of immunoproteasome subunits LMP2 and LMP7 is required to block autoimmunity. EMBO Rep., Dec. 2018. 19(12):e46512.
Behravesh, S. et al., "Venous malformations: clinical diagnosis and treatment. Cardiovascular diagnosis and therapy", Cardiovascular Diagnosis and Therapy, vol. 6 / Issue 6, pp. 557-569, Dec. 2016.
Brown et al., Pharmacokinetics of carfilzomib in patients with advanced malignancies and varying degrees of hepatic Impairment: an open-label, single-arm, phase 1 study. Exp hematol Oncol, Jul. 25, 2017. 6: 27.
Chen et al., Disulfiram, a clinically used anti-alcoholism drug and copper-binding agent, induces apoptotic cell death in breast cancer cultures and xenografts via inhibition of the proteasome activity. Cancer Res. Nov. 1, 2006. 66(21): 10425-33.

(Continued)

*Primary Examiner* — Lianko G Garyu
(74) *Attorney, Agent, or Firm* — Leason Ellis LLP

(57) ABSTRACT

Provided herein are methods and compositions for treating and preventing vascular malformations including lymphatic, venous, capillary, arteriovenous, and combinations thereof. Methods of treatment and prevention include the administration of proteasome inhibitors, omipalisib, disulfiram, and agents which target genes in the PI3K/AKT/mTOR or RAS/RAF/MAPK pathways, including but not limited to Pik3ca, Pik3r3, Tsc2, Rasa1, Map2k2, and Glmn.

6 Claims, 20 Drawing Sheets

(56) References Cited

OTHER PUBLICATIONS

Chen and Dou, New uses for old copper-binding drugs: converting the pro-angiogenic copper to a specific cancer cell death inducer. Expert Opin. Ther. Targets Jun. 2008. 12(6): 739-48.
Dompmartin et al., Association of localized intravascular coagulopathy with venous malformations. Arch Dermatol, Jul. 2008. 144(7): 873-7.
Foster et al., Kaposiform lymphangiomatosis effectively treated with MEK inhibition. EMBO Mol Med, Oct. 2020. 12 (10): e12324.
Gallerani et al., A first in human phase I study of the proteasome inhibitor CEP-18770 in patients with advanced solid tumours and multiple myeloma. Eur J Cancer Jan. 1, 2013, 49: 290-296.
Greene and Vascular Anomalies: From a Clinicohistologic to a Genetic Framework. Plast Reconstr Surg, May 2018. 141(5): 709e-717e.
Gupta et al., Pharmacokinetics of ixazomib, an oral proteasome inhibitor, in solid tumour patients with moderate or severe hepatic impairment. Br J Pharmacol Jan. 28, 2016. 82: 728-38.
Hammill et al., Sirolimus for the treatment of complicated vascular anomalies in children. Pediatr Blood Cancer, 2011. 57(6): 1018-24. Received Dec. 14, 2010.
Hari et al., Efficacy and safety results from a phase 1b/2, multi-center, open-label study of oprozomib and dexamethasone in patients with relapsed and/or refractory multiple myeloma. Leukemia Res Aug. 2019. 83: 106172.
Harrison et al., Phase I Clinical Trial of Marizomib (NPI-0052) in Patients with Advanced Malignancies Including Multiple Myeloma: Study NPI-0052-102 Final Results. Clin Cancer Res Sep. 15, 2016. 22: 4559-66.
Infante et al., A first-in-human dose-escalation study of the oral proteasome inhibitor oprozomib in patients with advanced solid tumors. Invest New Drugs Apr. 2016., 34: 216-224.
Lopez Gutierrez et al., Alpelisib Treatment for Genital Vascular Malformation in a Patient with Congenital Lipomatous Overgrowth, Vascular Malformations, Epidermal Nevi, and Spinal/Skeletal Anomalies and/or Scoliosis (Cloves) Syndrome. J Pediatr Adolesc Gynecol, 2019. 32(6): 648-650.
Lukey et al., A randomized, placebo-controlled study of omipalisib (PI3K/mTOR) in idiopathic pulmonary fibrosis. European Resp. Jour., 2019. 53: 1801992. Received Aug. 2, 2018.
Nikolaev et al., Somatic Activating KRAS Mutations in Arteriovenous Malformations of the Brain. N Engl J Med, Jan. 3, 2018. 378(3): 250-261.

Ou et al., Physiologically-based pharmacokinetic modelling to predict oprozomib CYP3A drug-drug interaction potential in patients with advanced malignancies. Br J Pharmacol 2019. 85: 530-539. Received Jul. 12, 2018.
Teicher and Tomaszewski, Proteasome inhibitors. Biochem Pharmacol, Jul. 2015. 96(1): 1-9.
Shabaneh et al. Molecular Basis of Differential Sensitivity of Myeloma Cells to Clinically Relevant Bolus Treatment with Bortezomib. PLoS One., Feb. 2013.
Uller, et al., Arteriovenous malformations. Semin Pediatr Surg, Aug. 2014. 23(4): 203-7.
Hammer, J et al., "Sirolimus is efficacious in treatment for extensive and/or complex slow-flow vascular malformations: a monocentric prospective phase II study", Orphanet Journal of Rare Diseases, vol. 13 / Issue 1, p. 191, Oct. 2018.
Lu et al., "Propranolol as a potentially novel treatment of arteriovenous malformations", JAAD Case Reports, vol. 4 / Issue 4, pp. 355-358, May 2018.
Ola R, Dubrac A et al., "PI3 kinase inhibition improves vascular malformations in mouse models of hereditary haemorrhagic telangiectasia", Nature Communications, vol. 7, Nov. 2016.
Venot Q et al., "Targeted therapy in patients with PIK3CA-related overgrowth syndrome", Nature, vol. 558 / Issue 7711, pp. 540-546, Jun. 2018.
Davis RB et al., "Notch signaling pathway is a potential therapeutic target for extracranial vascular malformations", Scientific Reports, vol. 8 / Issue 1, Dec. 2018.
Di Blasio L et al, "PI3K/mTOR inhibition promotes the regression of experimental vascular malformations driven by PIK3CA-activating mutations", Cell Death & Disease, vol. 9 / Issue 2, p. 45, Jan. 2018.
Horton et al., "Bortezomib Reinduction Chemotherapy in High-Risk ALL in First Relapse: A Report from the Children's Oncology Group", Br J Haematol. Jul. 2019 ; 186(2): 274-285. doi:10.1111/bjh.15919.
Bertaina et al., "The combination of bortezomib with chemotherapy to treat relapsed/refractory acute lymphoblastic leukaemia of childhood", British Journal of Haematology, 2017, 176, 629-636, Jan. 24, 2017.
Alpenc et al., "Bortezomib with standard chemotherapy for children with acute myeloid leukemia does not improve treatment outcomes: a report from the Children's Oncology Group", haematologica, vol. 105(7):1879-1886, Received Mar. 7, 2019.

* cited by examiner

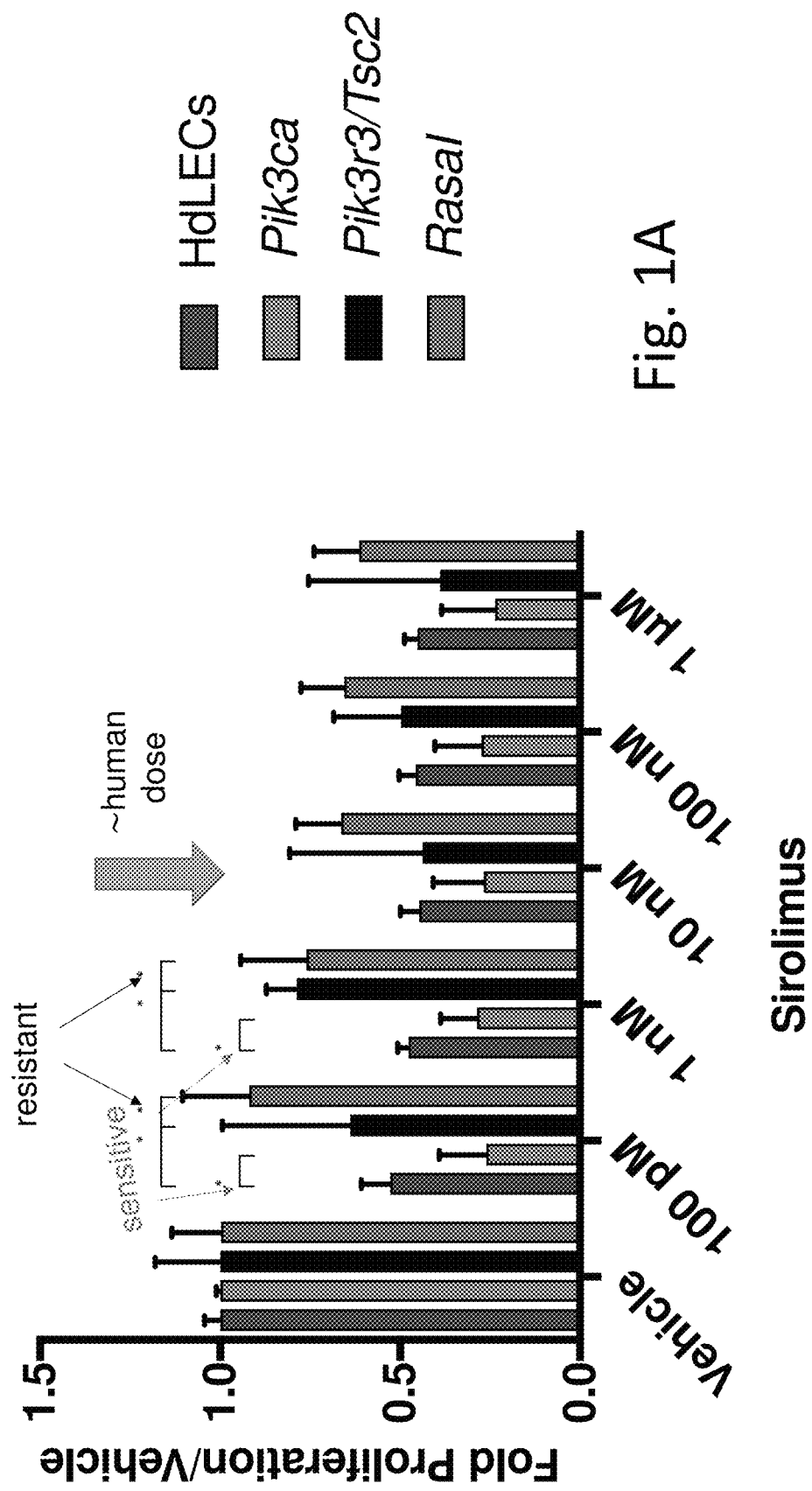

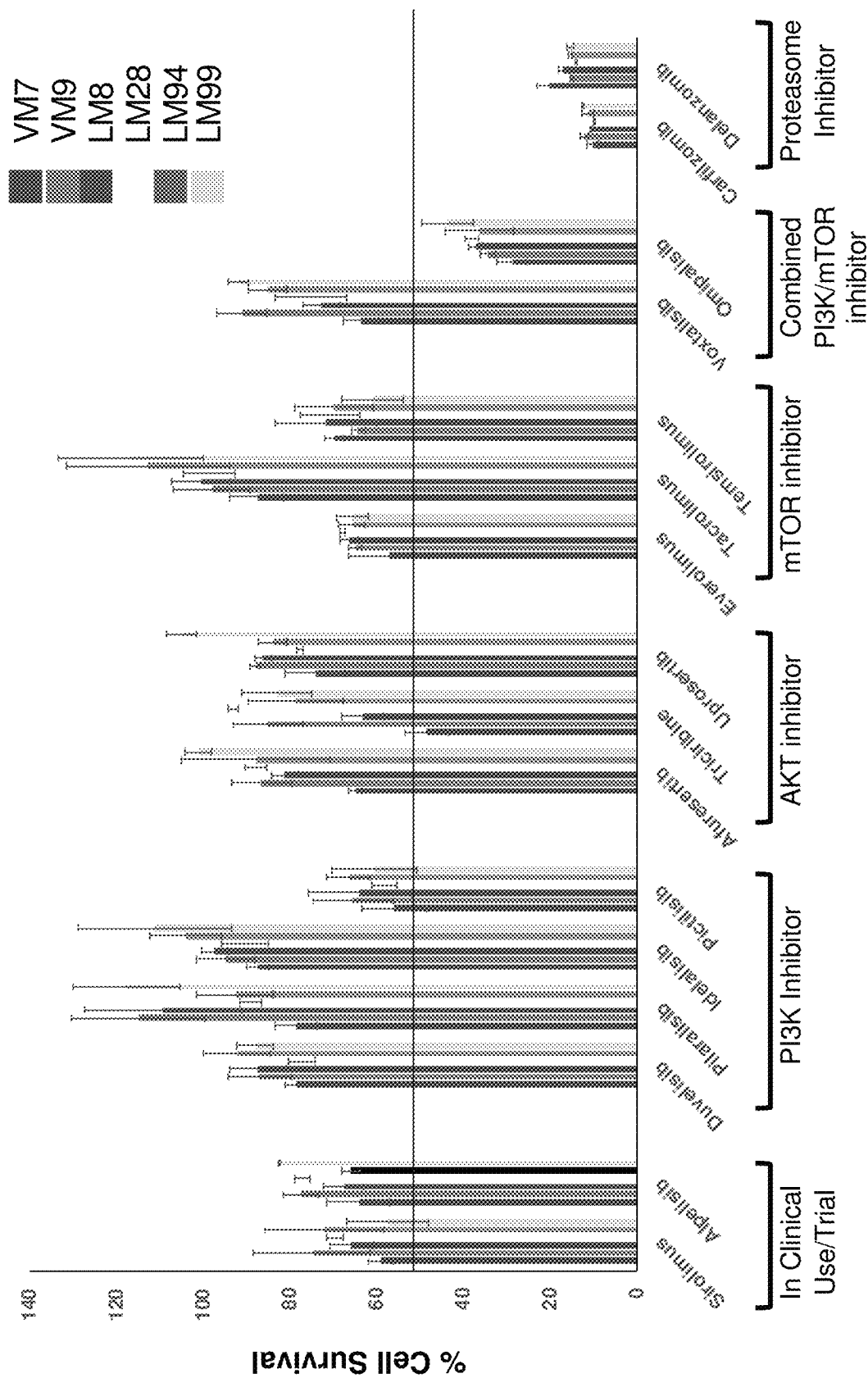

COMPOSITIONS AND METHODS FOR THE TREATMENT AND PREVENTION OF VASCULAR MALFORMATIONS

CROSS REFERENCE TO RELATED APPLICATION

The present application is a U.S. National Phase Application under 35 U.S.C. § 371 of International Patent Application No. PCT/US2021/032374, filed May 14, 2021, which claims priority to U.S. Patent Application Ser. No. 63/024,670, filed May 14, 2020, each of which is hereby incorporated by reference as if expressly set forth in their respective entirety herein.

STATEMENT OF GOVERNMENTAL INTEREST

This invention was made with government support under W81XWH-19-1-0266, and W81XWH-19-1-0267 awarded by the United States Army Medical Research and Development Command, and HD092662 awarded by the National Institutes of Health. The government has certain rights in the invention.

FIELD

This disclosure is in the field of preventing and treating vascular malformations, as well as in the field of screening for agents which prevent and treat these vascular malformations.

BACKGROUND

Vascular malformations are congenital anomalies of the blood and lymphatic vascular systems with a prevalence ranging from 1:3000 for lymphatic malformations (LMs) to 1% for venous malformations (VMs) and classified by the affected vessel type; capillary (CM), lymphatic (LM), venous (VM), and arteriovenous (AVM) malformations (Greene and Goss 2018; Behravesh et al. 2016). Vascular malformations are often apparent at birth and affected patients have significant morbidities and even mortality. Lymphatic dysfunction in LMs leads to defects in immune surveillance and lipid absorption leading to repeat infections and sepsis to malabsorption (Potente and Makinen 2017). VMs are associated with hematologic anomalies and painful intravascular coagulopathy (Dompmartin et al. 2008). In combined lymphatic and venous malformations (LVMs), deep vein thrombosis can result in life-threatening pulmonary emboli (Mazereeuw-Hautier et al. 2007). AVMs are associated with potentially life-threatening bleeding and heart failure (Uller et al. 2014). Another co-morbidity that affects all types of vascular malformation is hemorrhaging that can require repeated transfusions. In sensitive locations such as the brain, VMs and AVMs can have neurologically devastating consequences that can lead to death (Nikolaev et al. 2018). Despite these severe morbidities, there are no FDA-approved treatment for any vascular malformations.

Currently available treatments (such as surgery and interventional procedures) alleviate symptoms, but are not curative, and recurrence is common often requiring repeat interventions (Greene and Goss 2018; Behravesh et al. 2016). When the malformation is extensive, the effects of these treatments are limited at best. More recently, vascular malformation treatments have been guided by the genetics of the malformation. Studies have shown both germline and postzygotic genetic variants leading to hyperactivation of the PI3K/AKT/mTOR and/or the RAS/RAF/MAPK signaling pathways contribute to vascular malformation pathogenesis (Greene and Goss 2018). Based on this knowledge, pharmacotherapies—often cancer drugs—targeting these pathways have been used off-label clinically. Sirolimus, an mTOR inhibitor targeting the PI3K/AKT hyperactivation, has been used most extensively for VMs and LMs, but has generated only partial response (Hammill et al. 2011).

More recently, there have been multiple anecdotal reports using alpelisib, a Pik3ca inhibitor which targets PI3K/AKT/mTOR hyperactivation (Lopez Gutierrez et al. 20191), and trametinib, a MEK inhibitor targeting hyperactivated RAS/RAF/MAPK pathway hyperactivation (Foster et al. 2020). However, no pharmacotherapy, or class of pharmacotherapies, have shown complete response, despite this targeted approach.

Development of effective, biologically targeted therapies is sorely needed, but hampered by our limited understanding of how their genetics influences therapeutic responses.

SUMMARY

Using high throughput screening of endothelial cells from patients with vascular malformations, which had been identified as having specific genetic mutations, pharmacological agents were identified which inhibited the growth and viability of the cells. These pharmacological agents can be used for the treatment and prevention of vascular malformations, as well as to develop therapeutic and preventative agents for vascular malformations.

Thus, one embodiment of the present disclosure is a method of preventing and/or treating vascular malformations, comprising administering to a subject in need thereof a therapeutically effective amount of a proteasome inhibitor.

In some embodiments, the proteasome inhibitor is an inhibitor of the 20s subunit of proteasomes. In some embodiments, the proteasome inhibitor is an inhibitor of the chymotrypsin-like activity (CT-L), trypsin-like activity (T-L) and/or caspase-like (C-L) activity of the 20s subunit. In some embodiments, the proteasome inhibitor is an inhibitor of all three activities. In some embodiments, the proteasome inhibitor is an inhibitor of two of the three activities. In some embodiments, the proteasome inhibitor is an inhibitor of one of the three activities. In some embodiments, the proteasome inhibitor is an inhibitor of chymotrypsin-like activity of the 20s subunit.

In some embodiments, the proteasome inhibitor acts indirectly to inhibit proteolytic activities of proteasome complex.

In some embodiments, the proteasome inhibitor is listed in Tables 1 and 2.

The proteasome inhibitor for use in the method includes but is not limited to carfilzomib, delanzomib, ixazomib, bortezomib, oprozomib, and marizomib. See Table 1.

Additional proteasome inhibitors for use in the method include but are not limited to those listed in Table 2.

A further embodiment of the present disclosure is a method of preventing and/or treating vascular malformations, comprising administering to a subject in need thereof a therapeutically effective amount of disulfiram.

A further embodiment of the present disclosure is a method of preventing and/or treating vascular malformations, comprising administering to a subject in need thereof a therapeutically effective amount of an agent or compound which has proteasome inhibiting ability.

A further embodiment of the present disclosure is a method of preventing and/or treating vascular malformations, comprising administering to a subject in need thereof a therapeutically effective amount of a copper-binding agent or compound.

A further embodiment of the present disclosure is a method of preventing and/or treating vascular malformations, comprising administering to a subject in need thereof a therapeutically effective amount of omipalisib.

A further embodiment of the present disclosure is a method of preventing and/or treating vascular malformations, comprising administering to a subject in need thereof a therapeutically effective amount of an agent which targets a mutation in a gene chosen from the group consisting of Pik3ca, Pik3r3, Tsc2, Rasa1, Map2k2, Glmn, and combinations thereof.

A further embodiment of the present disclosure is a method of preventing and/or treating vascular malformations, comprising administering to a subject in need thereof a therapeutically effective amount of an agent which targets a mutation in a gene in the PI3K/AKT/mTOR or RAS/RAF/MAPK pathway. Such genes include but are not limited to Kras and Nras.

Vascular malformations that can be prevented and/or treated by the disclosed methods include but are not limited to lymphatic malformations (LMs), venous malformations (VMs), capillary malformations (CM), arteriovenous malformations (AVM), and combinations thereof.

In some embodiments, the agent further comprises a pharmaceutically acceptable carrier and is part of a composition.

In some embodiment, the subject is over 18 years old. In some embodiments, the subject is under 18 years old. In some embodiments, the subject is under 16 years old. In some embodiments, the subject is under 10 years old. In some embodiments, the subject is under 5 years old. In some embodiments, the subject is under 1 year old.

In an additional embodiment, the disclosure provides for methods of obtaining cells from the vascular malformation of the subject and testing the efficacy and/or dosage of any agent prior to administration of the agent. In some embodiments, these cells are endothelial cells. In some embodiments, the cells are subject to sequencing or other analysis to determine the mutations and/or defects within the cells.

A further embodiment of the present disclosure are kits comprising compositions and agents for practicing the disclosed methods.

A further embodiment of the present disclosure is a method and/or assay for screening and/or identifying an agent for the treatment and/or prevention of vascular malformations including lymphatic, venous, capillary, and arteriovenous and combinations thereof, comprising contacting or incubating a test agent with a cell derived from a patient with a vascular malformation, wherein if the viability and/or proliferation of the cells is decreased after contact or incubation with the test agent, the test agent is identified as a therapeutic and/or preventative agent for vascular malformations.

In some embodiments, the cells are endothelial cells. In some embodiments, the cells harbor mutations in a gene in the PI3K/AKT/mTOR or RAS/RAF/MAPK pathway. In some embodiments, the cells harbor mutations in a gene chosen from the group consisting of Pik3ca, Pik3r3, Tsc2, Rasa1, Map2k2, Glmn, and combinations thereof. In some embodiments, the cells are chosen from the group of cells listed in Table 3. In some embodiments, high throughput screening is performed. In some embodiments, the cells are subject to sequencing or other analysis to determine the mutations and/or defects within the cells.

The disclosure also includes any agents identified by the screening methods described herein and methods of using the same for the prevention and/or treatment of vascular malformations including lymphatic, venous, capillary, and arteriovenous and combinations thereof.

BRIEF DESCRIPTION OF THE FIGURES

For the purpose of illustrating the invention, there are depicted in drawings certain embodiments of the invention. However, the invention is not limited to the precise arrangements and instrumentalities of the embodiments depicted in the drawings.

FIG. 1—Inhibitors that target the PI3K/AKT and RAS/MAPK pathways display different efficacies against LMECs. FIG. 1A shows the results of LMECs with different genetic variants (PIK3CA, PIK3CA/TSC2, and RASA1) and control cells (HdLECs) treated with increasing log doses of sirolimus.

FIG. 2—PI3K/AKT pathway inhibitors differentially affect cell survival in a HTPS assay. Six endothelial cell populations isolated from venous malformation (VM) and lymphatic malformation (LM) patients (VMECs and LMECs), carrying mutations that hyperactivate PI3K signaling, were subjected HTPS with all inhibitors at 1 µM. Cell survival was determined after 48 hours and data presented as percent cell survival of cells treated with 1 µM compound versus vehicle-treated control±SD. Small molecules presented belonged to 2 classes of inhibitors: PI3K inhibitors and proteasome inhibitors (right). Dark gray line: 50% cell from starting number. Omipalisib and proteasome inhibitors were significantly more efficacious than sirolimus at inhibiting growth/survival of the ECs with PI3K hyperactivation. Sirolimus to PI3K/mTOR inhibitors: ANOVA $p=0.0017$, post-hoc TTEST sirolimus vs. omipalisib $p=0.0005$. Sirolimus vs proteasome Inhibitors: ANOVA $p=0.0013$, post-hoc TTEST sirolimus vs. carfilzomib $p<0.0001$, sirolimus vs. delanzomib $p=0.0093$.

FIG. 4 is a graph of cell viability of treated cells relative to vehicle treated cells. Using HTPS, VMEC/LMECs carrying variants in genes in the RAS/RAF/MAPK (LMEC10, VMEC13) or PI3K/AKT/mTOR (VMEC7/9, LMEC8/28/94/99) pathways (Table 3) were treated with 1 µM of 1344 compounds. Cell viability relative to vehicle treated cells was determined after 48 hours. Data presented for three PIs tested, and sirolimus, alpelisib, and trametinib, all of which have been used off label for vascular malformation patients.

FIG. 5—Dose Response Curves of PIs, sirolimus, alpelisib and omipalisib using HMVEC (n=2) (control/ normal/wild-type cells to be compared to those from vascular malformation patients), VMEC7, VMEC9, LMEC94 and LMEC99 (Table 3). The graphs show the percent viability of the cells at the various doses in μM (dose range, 0.00125 μM to 20 μM). The large arrows mark the reported plasma concentration in humans. FIG. 5A shows marizomib.

FIG. 6 is a graph of the results of VMECs (n=2) and LMECs (n=2) carrying Pik3ca mutations subjected to increasing amounts of designated PI (left 6) or sirolimus or alpelisib, and cell viability determined after 48 hours at doses corresponding to clinically reported plasma concentration in μM. Data represent plasma concentration achieved in humans and presented as % viable cells treated with drug relative to vehicle treated cells.

FIG. 7 is a graph of the results of LMEC28 carrying Pik3r3;Tsc2 mutations subjected to increasing amounts of oprozomib and cell viability determined after 48 hours. Yellow arrow marks clinically relevant dose and presented as % viable cells treated with drug relative to vehicle treated cells.

FIG. 8—In vivo testing of PIs. In a xenograft model, oprozomib inhibited VM vessel growth.

DETAILED DESCRIPTION

Definitions

Figure 1B:
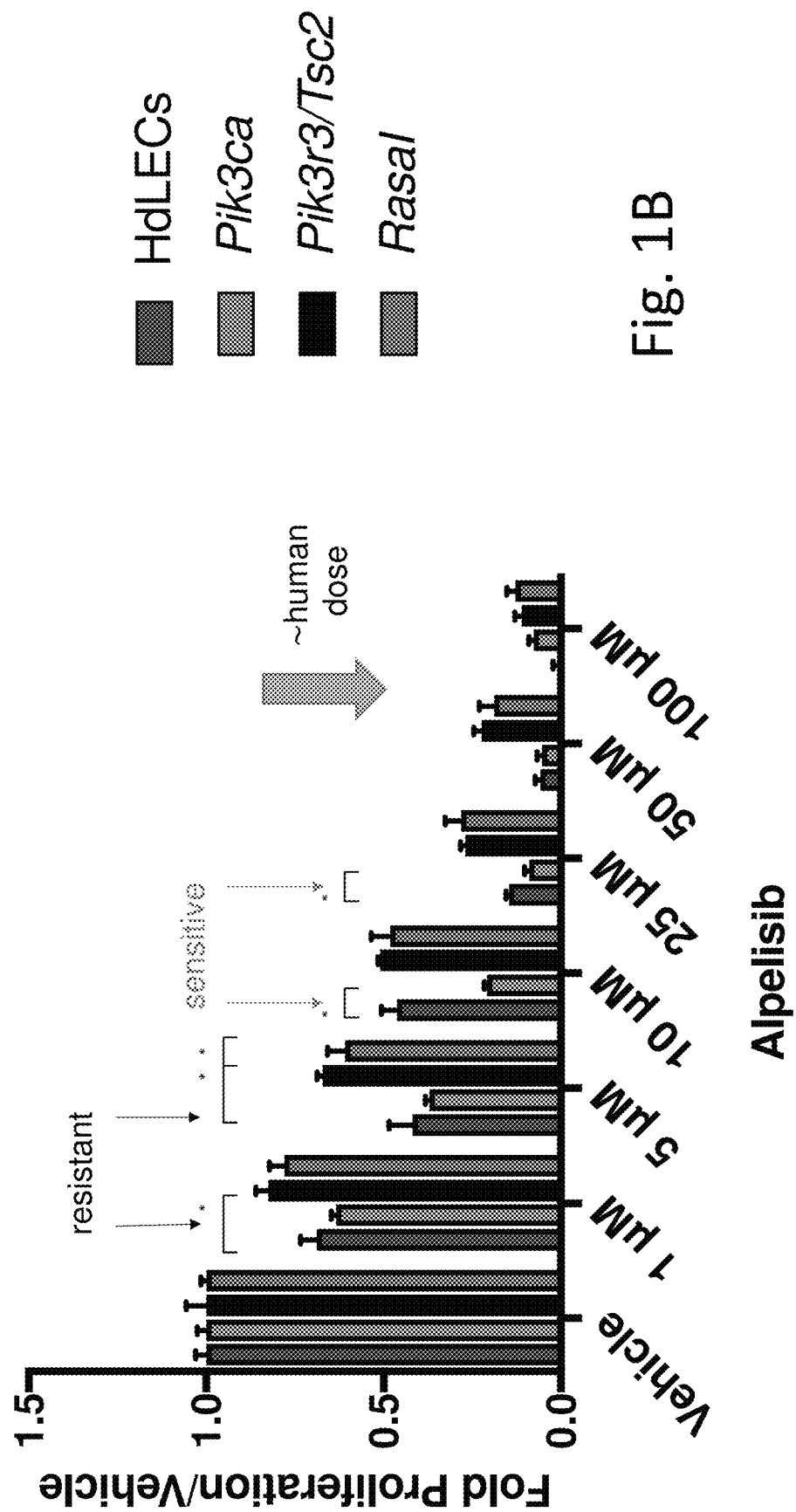
FIG. 1B shows the results of the same cells treated with increasing log doses of alpelisib.

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications.

The term "patient" as used in this application means a human subject. In some embodiments of the present invention, the "patient" is suffering with from a vascular malformation, or a disease or condition characterized by a vascular malformation including capillary (CM), lymphatic (LM), venous (VM), and arteriovenous (AVM), and combinations thereof.

The terms "treat", "treatment", and the like refer to a means to slow down, relieve, ameliorate or alleviate at least one of the symptoms of the disease, or reverse the disease after its onset.

The terms "prevent", "prevention", and the like refer to acting prior to overt disease onset, to prevent the disease from developing or minimize the extent of the disease or slow its course of development.

The term "in need thereof" would be a subject known or suspected of having or being at risk of a vascular malformation or a disease or condition characterized by a vascular malformation including capillary (CM), lymphatic (LM), venous (VM), and arteriovenous (AVM), and combinations thereof.

A subject in need of treatment would be one that has already developed the disease or condition. A subject in need of prevention would be one with risk factors of the disease or condition.

The term "agent" as used herein means a substance that produces or is capable of producing an effect and would include, but is not limited to, chemicals, pharmaceuticals, biologics, small organic molecules, antibodies, nucleic acids, peptides, and proteins.

The phrase "therapeutically effective amount" is used herein to mean an amount sufficient to cause an improvement in a clinically significant condition in the subject, or delays or minimizes or mitigates one or more symptoms associated with the disease, or results in a desired beneficial change of physiology in the subject.

The terms "screen" and "screening" and the like as used herein means to test an agent to determine if it has a particular action or efficacy.

The terms "identification", "identify", "identifying" and the like as used herein means to recognize an agent as being effective for a particular use.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Abbreviations

LM lymphatic malformation
VM venous malformation
CM capillary malformation
AVM arteriovenous malformation
EC s endothelial cells
LMECs lymphatic malformation endothelial cells
VMECs venous malformation endothelial cells
HMVECs human microvascular endothelial cells (controls)
WES whole exome sequencing
HTPS high throughput screening
PI proteasome inhibitor Identification of Therapeutic and Prophylactic Agents for Vascular Malformations Germline mutations have been identified in some vascular malformation subtypes yet screening for germline variants has often failed to identify causative mutations. Recent studies have shown that post-zygotic mutations contribute to a significant portion of AVMs, VMs, and LMs. Somatic mutations are present only in affected tissues, specifically the malformed endothelial cells (ECs).

Endothelial cells from vascular malformation tissues carrying known disease associated pathogenic variants, including those that target the PI3K/AKT/mTOR and RAS/RAF/MAPK pathways were collected. It was hypothesized that ECs isolated from patients that carried pathogenic somatic, as well as yet to be identified variants, could be used in a drug screen to identify novel therapies for the treatment of vascular malformations. Whole exome sequencing (WES) was used in the patient derived endothelial cells from venous and lymphatic malformation patients to identify mosaic pathogenic variants. These cells were then used in high throughput drug screening (HTPS) to identify new potential therapies for the venous and lymphatic malformation population (Table 3).

Using these endothelial cells carrying variants leading to activation of the PI3K pathway in HTPS, omipalisib, a combined PI3K/mTOR inhibitor, as well as proteasome inhibitors, as a class, and disulfiram, were identified to be efficacious in inhibiting cell survival. In the HTPS and proliferation assays, omipalisib and proteasome inhibitors, as well as disulfiram, had significantly improved efficacy when compared to sirolimus and alpelisib which are the standard of care for patients with vascular malformations.

Methods and Compositions for the Prevention and Treatment of Vascular Malformations Based upon the findings set forth herein, the present disclosure provides for methods of preventing and/or treating vascular malformations including lymphatic, venous, capillary, arteriovenous, and combinations thereof, comprising administering to a subject in need thereof a therapeutically effective amount of an agent which targets a mutation in a gene in the PI3K/AKT/mTOR or RAS/RAF/MAPK pathway.

The current disclosure further provides for methods of preventing and/or treating vascular malformations including lymphatic, venous, capillary, arteriovenous, and combinations thereof, comprising administering to a subject in need thereof a therapeutically effective amount of an agent which targets a mutation in a gene chosen from the group consisting of Pik3ca, Pik3r3, Tsc2, Rasa1, Map2k2, Glmn, and combinations thereof.

The current disclosure further provides for methods of preventing and/or treating vascular malformations including lymphatic, venous, capillary, arteriovenous, and combinations thereof, comprising administering to a subject in need thereof a therapeutically effective amount of omipalisib.

HTPS determined that omipalisib was the strongest PI3K pathway inhibitor of proliferation/viablity of vascular malformation endothelial cells with PI3K hyperactivation, relative to the 14 tested inhibitors of the PI3K pathway. Omipalisib is a dual PI3K pathway inhibitor which targets the p110 activation domain of PI3K and MTOR, suggesting targeting two protein complexes in the PI3K pathway is more effective than a single target. When another dual PI3K and MTOR inhibitor, bimiralisib, or the clinically used sirolimus were assessed, omipalisib was significantly more efficacious at inhibiting proliferation of LMECs at a lower concentration then either of the other drugs.

Together these data suggest omipalisib is more effective at targeting the pathogenic hyperactivation of PI3K in vascular malformations than current therapies.

Omipalisib has completed Phase I clinical trials for both solid tumors (NCT00972686) and idiopathic pulmonary fibrosis (NCT01725139). It has never been investigated as a candidate for therapy for vascular malformations.

Without being bound by any theory, it is hypothesized that this drug uniquely inhibits the pathological hyperactivation of the PI3K signaling in two different subtypes of vascular malformations, venous and lymphatic malformations. Both vascular malformations have been shown to arise from somatic mutations endothelial cells in genes of the PI3K signaling pathway, including Pik3ca, Pik3r3, Tsc2, and Akt, which lead to increased activity of the PI3K p110 subunit and mTOR proteins targeted by omipalisib.

Omipalisib:
  formula: $C_{25}H_{17}F_2N_5O_3S$
  chemical name: 2,4-difluoro-N-(2-methoxy-5-(4-(pyridazin-4-yl)quinolin-6-yl)pyridin yl)benzenesulfonamide.
  Dose: 0.5 to 2 mg BID
  Effective concentration—74.6 ng/mL (=0.15 µM) (Lukey et al. 2019)

The current disclosure further provides for methods of preventing and/or treating vascular malformations including lymphatic, venous, capillary, arteriovenous, and combinations thereof, comprising administering to a subject in need thereof a therapeutically effective amount of one or more proteasome inhibitors. The disclosure further provides for methods of preventing and/or treating vascular malformations, including lymphatic, venous, capillary, arteriovenous, and combinations thereof, comprising administering to a subject in need thereof a therapeutically effective amount of an agent or compound which has proteasome inhibiting ability.

Proteasome inhibitors that can used in the method include but are not limited to bortezomib, oprozomib, carfilzomib, ixazomib, delanzomib, and marizomib.

Several proteasome inhibitors are already FDA-approved, while several are in different phases of clinical trials. The FDA-approved indication is for the treatment of multiple myeloma, while clinical trials are also investigating their use in solid tumors and non-Hodgkins lymphoma.

Proteasome inhibitors as a class has not been investigated for use in patients with vascular malformations. See Tables 1 and 2.

Some of the proteasome inhibitors identified target the 20S catalytic subunit in the proteasome complex and in some instances, target all three proteolytic activities of the 20S subunit including the chymotrypsin-like activity (CT-L), trypsin-like activity (T-L) and caspase-like (C-L) activity. In some instance, the PIs targeted the chymotrypsin-like activity. In some instances, the proteasome inhibitors act indirectly to inhibit the proteasome complex.

Mutations in genes that make up the proteasome complex or their involvement in vascular pathologies have not been reported for vascular malformations.

Without being bound by any theory, proteasomes function in protein degradation via autophagy and ubiquitin-dependent, or ubiquitin-independent proteasome degradation pathway and has been implicated as a regulator of PI3K signaling. Thus, proteasome inhibitors may also inhibit proliferation of vascular malformation cells by targeting genetic activation of the PI3K pathway.

Proteasomes have also been shown to modulate angiogenic signaling via regulation of VEGF-A/VEGFR2 signaling, as well as other angiogenic and lymphangiogenic pathways.

Additionally, disulfiram was also found to inhibit cell proliferation and viability. Disulfiram has shown inhibition of proteasome activity. Thus, the current disclosure further provides for methods of preventing and treating vascular malformations including lymphatic, venous, capillary, arteriovenous, and combinations thereof, comprising administering to a subject in need thereof a therapeutically effective amount of disulfiram.

Copper-binding compounds, such as disulfiram, Clioquinol and diethyldithiocarbamate have also been documented to have proteasome inhibiting ability (Chen et al. 2006; Chen and Dou 2008). Thus, current disclosure further provides for methods of preventing and/or treating vascular malformations including lymphatic, venous, capillary, arteriovenous, and combinations thereof, comprising administering to a subject in need thereof a therapeutically effective amount of a copper-binding agent or compound. Copper-binding agents or compounds for use in the current methods include but are not limited to NSC-109268, pyrrolidine dithiocarbamate, disulfiram, Clioquinol and diethyldithiocarbamate.

TABLE 1

FDA Approved Currently Available Proteasome Inhibitors

| Inhibitor | Mechanism | FDA Approval Status | Dose | Plasma Concentration (ng/mL) |
|---|---|---|---|---|
| Bortezomib | Selective, reversible inhibitor of chymotrypsin-like activity of the 20S proteasome | 2005 | 0.4-1.38 mg/m² | 100-200 (260-520 nM) (Shabaneh et al. 2013) |
| Carfilzomib | Irreversible epoxyketone inhibitor of the chymotrypsin-like activity of 20S | 2012 | 27-56 mg/m² | 932-2733 (1294-3796 nM) (Brown et al. 2017) |
| Marizomib | Irreversible inhibitor of all three proteasome protease activities (chymotrypsin-like, trypsin-like and caspase-like activity of 20S) | Orphan drug designation 2015 | 0.075-0.9 mg/m² | 2.76-57.75 (8.8-184 nM) (Harrison et al. 2016) |
| Izazomib (oral) | Boronic acid proteasome inhibitor of chymotrypsin-like activity of 20S | 2015 | 1.5-4 mg/d | 26.1-61 (72.3-169 nM) (Gupta et al. 2016) |
| Oprozomib (oral) | Irreversible tripeptide epoxyketone inhibitor of chymotrypsin-like activity of 20S (orally bioavailable analog of Carfilzomib) | Orphan drug designation 2014 | 240 mg/day (30-150 mg/d) | 218-870 (409-1633 nM) (Infante et al. 2016) |
| Delanzomib (IV or oral) | Inhibitor of the proteasome chymotrypsin-like activity of 20S that decreases NF-kB activity | Clinical trials | 0.1-1.8 mg/m² | 88.4-557.3 (214-1348 nM) (Gallerani et al. 2013) |

TABLE 2

Additional Proteasome Inhibitors

| Generic Name | Drug Name | Drug Disease | Mechanism of Action | Delivery Route | Notes |
|---|---|---|---|---|---|
| 4SC-206 | 4SC-206; SC-68896 | Cancer solid, unspecified; brain; myeloma | Proteasome inhibitor | Injectable | Injectable proteasome inhibitor, which was under development for the treatment of solid tumors and inflammation. Indications included multiple myeloma, small cell lung cancer and neurological tumors. Preclinical testing in colon cancer and glioblastoma. |
| ACU-D1 | ACCU D1; ACCUD1; ACCU-D1; ACU D1; ACUD1; ACU-D1 | Acne; dry eye syndrome; psoriasis; rosacea | Proteasome inhibitor Transcription factor NF-kappaB inhibitor | Topical | Nuclear factor kappa beta (NFkB) inhibitor, which was under development for the treatment of skin and ocular diseases including acne rosacea, psoriasis and acne. Phase II testing for acne rosacea. It was previously under development for dry eye |
| anticancer therapy, Teva | anticancer therapy, Teva | Cancer, unspecified | Proteasome inhibitor | | Teva was developing a series of (2S, 3R)-2-amino-3-hydroxy-butyric acid derived proteasome inhibitors, for the treatment of cancer |
| AVR-147 | AVR-147; CTK-000147; CTK-100147 | Cancer, unspecified | Proteasome inhibitor | | A novel, natural product small-molecule proteasome inhibitor, which was under development) for the treatment of cancer. It is highly selective for the |

TABLE 2-continued

Additional Proteasome Inhibitors

| Generic Name | Drug Name | Drug Disease | Mechanism of Action | Delivery Route | Notes |
|---|---|---|---|---|---|
| BSc-2118 | BSc-2118 | Cancer, lymphoma; unspecified; myeloma | Proteasome inhibitor; Apoptosis stimulant | | chymotrypsin-like activity of the proteasome. A novel tripeptide with inhibitory activity against the 3 proteolytic activities of the 20S proteasome, which was under development for the treatment of multiple myeloma (MM) and mantle cell lymphoma (MCL). |
| CEP-28331 | CEP-28331 | Cancer, myeloma | Proteasome inhibitor | Oral; Oral, swallowed | Oral proteasome inhibitor, which was under development for the treatment of multiple myeloma |
| CVT-857 | CVT-710; CVT-857 | Inflammatory disease, unspecified | Proteasome inhibitor | | CVT-857 and CVT-710 are alpha-ketoamide-terminated retropeptides, which were under investigation as potential anti-inflammatories. They selectively inhibit the chymotrypsin-like site of the 20S proteasome complex without inhibiting either the peptidylglutamyl- or trypsin-like proteolytic activities of the 20S complex, suggesting that the active site, threonine, in the 20S proteasome is not undergoing nucleophilic addition to |

TABLE 2-continued

Additional Proteasome Inhibitors

| Generic Name | Drug Name | Drug Disease | Mechanism of Action | Delivery Route | Notes |
|---|---|---|---|---|---|
| | | | | | the electrophilic carbonyl of the alpha-ketomide group. |
| CX13-608 | CX13 608; CX13608; CX13-608 | Cancer, myeloma; lymphoma; unspecified | Proteasome inhibitor | Injectable, intravenous | A proteasome inhibitor, under development for the treatment of multiple myeloma. Phase I and Phase II testing. |
| CYS-006 | anticancers, Cytomics Systems; CYS-006 | Cancer, unspecified | Proteasome inhibitor | | CYS-006 was a series of compounds targeting the ubiquitin-proteasome protein degradation pathway, under development as proteasome inhibitors to stabilize the degradation of a protein that has been implicated in the pathogenesis of malignancies. |
| disulfiram + copper, Cantex | CX 02; CX02; CX-02; Dicopp; disulfiram + copper gluconate, Cantex; disulfiram + copper, Cantex | Cancer, pancreatic; myeloma; sarcoma; unspecified brain; breast; lung, non-small cell; prostate, Poisoning, radiation | Chemokine receptor antagonist; Proteasome inhibitor | Oral; Oral, swallowed | Dicopp (CX-02) is an oral, single-dose combination of disulfiram + copper, under development for the treatment of pancreatic cancer, pediatric sarcoma and myeloma. It was previously under development for brain, prostate, lung and breast cancers. Phase I and Phase II testing of some cancers. |
| ER-807446 | ER-804191; ER-807446 | Cancer, unspecified | Proteasome inhibitor | | A representative compound in a series of epoxyketone derivatives based on the |

TABLE 2-continued

Additional Proteasome Inhibitors

| Generic Name | Drug Name | Drug Disease | Mechanism of Action | Delivery Route | Notes |
|---|---|---|---|---|---|
| | | | | | natural product eponemycin, which was under investigation as proteasome inhibitors for the treatment of cancer. |
| FV-162 | anticancer therapy, Fluorinov Pharma; FV162; FV-162 | Cancer, lymphoma, non-Hodgkin's Cancer, myeloma | Proteasome inhibitor | Oral; Oral, swallowed | A potent, orally-delivered small molecule proteasome inhibitor, was under development for the treatment of multiple myeloma. It is a novel fluorine-based therapy. Fluorine atoms are introduced in to drug candidates to modify the specific physical and chemical properties of the parent drug molecules. It works by selectively inhibiting the chymotrypsin-like enzymatic activity of the proteasome. Phase I testing in myeloma. |
| FV-214 | FV214; FV-214 | Cancer, myeloma Waldenstrom's hypergamma-globulinaemia | Proteasome inhibitor | Injectable, intravenous | A potent, intravenously (iv) delivered small molecule proteasome inhibitor, which was under development for the treatment of multiple myeloma, Waldenstrom's macroglobulin-aemia. It works by selectively inhibiting the chymotrypsin-like enzymatic |

TABLE 2-continued

Additional Proteasome Inhibitors

| Generic Name | Drug Name | Drug Disease | Mechanism of Action | Delivery Route | Notes |
|---|---|---|---|---|---|
| G4-1 | G4 1; G4-1 | Cancer, solid; unspecified | Proteasome inhibitor | | activity of the proteasome. A novel proteasome inhibitor, under development for the treatment of solid tumors. |
| GNF-6702 | GNF6702; GNF-6702 | Infection, leishmaniasis; trypanosomiasis | Proteasome inhibitor | | A selective inhibitor of the kinetoplastid proteasome which was under development for the treatment of leishmaniasis, Chagas disease and sleeping sickness. |
| GSK439 | | | Proteasome inhibitor | | |
| GSK-3494245 | DDD 1305143; DDD1305143; DDD-1305143; GSK 3494245; GSK3494245; GSK-3494245; GSK3494245/DDD 1305143, DNDi; GSK3494245/DDD 1305143, GlaxoSmithKline | Infection, leishmaniasis | Proteasome inhibitor | Oral; Oral, swallowed | Under development for the treatment of Leishmaniasis. Phase I testing. |
| immuno-proteasome inhibitors, Principia BioPharma | immunoproteasome inhibitors, AbbVie; immunoproteasome inhibitors, Principia BioPharma | Autoimmune disease, Inflammatory disease | Proteasome inhibitor | Oral; Oral, swallowed | Oral immuno-proteasome inhibitors, for the treatment of inflammatory disease and autoimmune disorders such as inflammatory bowel diseases (IBD), lupus and psoriasis. It was previously under development for the treatment of immunological disease. Some are LMP2 and LMP7 inhibitors (Basler et al. 2018). |
| KZR-616 | KZR616; KZR-616; KZR616 (IV); KZR-616 (IV); KZR616 (SC); KZR-616 (SC); ONX 0914; ONX-0914; ONYX0914; | Autoimmune disease, Inflammatory disease | Proteasome inhibitor | Injectable; Injectable, intravenous; Injectable, subcutaneous | Selective small molecule inhibitor of the immuno-proteasome, under |

TABLE 2-continued

Additional Proteasome Inhibitors

| Generic Name | Drug Name | Drug Disease | Mechanism of Action | Delivery Route | Notes |
|---|---|---|---|---|---|
| | ONYX-0914; PR957; PR-957 | | | | development for the treatment of autoimmune diseases and inflammatory diseases. Phase I and Phase II testing. |
| LGP-07154 | LGP07154; LGP-07154; VAL-789-CHUM | Cancer, unspecified Immunological disease, unspecified | Proteasome inhibitor unspecified | Oral; Oral, swallowed | |
| LMP7 inhibitor, Shouyao Holdings | LMP7 inhibitor, Shouyao Holdings | Cancer, hematological; unspecified, Autoimmune disease, unspecified, Inflammatory disease | proteasome subunit beta type-8 inhibitor | Oral; Oral, swallowed | |
| LODO-141 | TIR199, TIR 199, LODO141, LODO 141,TIR-199 | Solid Tumors | | | LODO-141 (TIR-199) is an irreversible and potent hybrid cyclic peptide proteasome inhibitor from the syrbactin natural product family. |
| LXE-408 | LXE 408; LXE408; LXE-408 | Infection, leishmaniasistry-panosomiasis, American | Proteasome inhibitor | Oral; Oral, swallowed | Proteasome inhibitor, under development for the treatment of visceral leishmaniasis. It was previously under development for Chagas disease. Phase I and Phase II testing. |
| M-3258 | M 3258; M3258; M-3258 | Cancer, myeloma | Proteasome subunit beta type-8 inhibitor | Oral; Oral, swallowed | Immuno-proteasome subunit LMP7 inhibitor under development for the treatment of multiple myeloma. Phase 1 testing. |
| MCIT-375 | Anti-CD38/bortezomib/lenalidomide Dual Drug Pay load ADC; MCIT375; MCIT-375 | Cancer, myeloma | Proteasome inhibitor; Cereblon E3 ubiquitin ligase stimulant; Angiogenesis inhibitor; Immuno- | Injectable | An anti-CD38 antibody drug conjugate with dual drug payloads bortezomib and lenalidomide, |

TABLE 2-continued

Additional Proteasome Inhibitors

| Generic Name | Drug Name | Drug Disease | Mechanism of Action | Delivery Route | Notes |
|---|---|---|---|---|---|
| | | | oncology therapy | | which was under development for the treatment of multiple myeloma. |
| MLN519 | | Inflammatory Disease and Stroke | Ubiquitin Proteasome inhibitor | | Phase I and Phase II testing |
| OSH-101 | OSH-101 | Alopecia | Proteasome inhibitor | Topical; Topical, skin | A tetrapeptide aldehyde proteasome inhibitor, which was under development for the treatment of male and female pattern baldness and chemotherapy-induced alopecia. Other possible indications include alopecia areata, age-related hair thinning and post-transplant hair regrowth. Phase I testing complete, Phase II planned. |
| peptide epoxyketones, Onyx Pharmaceuticals | peptide epoxyketones, Onyx Pharmaceuticals | Inflammatory disease, unspecified | Proteasome inhibitor | | Subunit selective peptide epoxyketones as proteasome inhibitors, for the treatment of inflammatory disease. |
| proteasome inhibitor, Flaveome | proteasome inhibitor, Flaveome | Cancer, unspecified | Proteasome inhibitor | Oral; Oral, swallowed | A next generation orally-bioavailable proteasome inhibitor for the treatment of cancer. It also inhibits PI3K/Akt signalling. They are small molecules derived from flavonoid structures. |
| proteasome inhibitors, EntreMe | proteasome inhibitors, EntreMe | Cancer, unspecified | Proteasome inhibitor | | Small-molecule proteasome |

TABLE 2-continued

Additional Proteasome Inhibitors

| Generic Name | Drug Name | Drug Disease | Mechanism of Action | Delivery Route | Notes |
|---|---|---|---|---|---|
| | | | | | inhibitors, for the treatment of cancer. |
| proteasome inhibitors, Ergon Pharmaceuticals | proteasome inhibitors, Ergon Pharmaceuticals | Cancer, unspecified | Proteasome inhibitor | | Novel 26S proteasome inhibitors, for the treatment of cancer. |
| proteasome inhibitors, Jeil | proteasome inhibitors, Jeil | Cancer, unspecified | Proteasome inhibitor | | |
| proteasome inhibitors, NYU | proteasome inhibitors, NYU | Infection, malaria | Proteasome inhibitor | | Inhibitors of enzymes of the ubiquitin-proteasome pathway, different from those of the PS-341 series (qv), for the treatment of malaria and other parasitic diseases. The pathway is involved in proteolysis which occurs during Plasmodium falciparum's lifecycle (Scrip, 1997, 2239, 19). |
| proteasome inhibitors, QLi5 Therapeutics | proteasome inhibitors, QLi5 Therapeutics | Autoimmune disease, unspecified Cancer, unspecified Inflammatory disease, unspecified | Proteasome inhibitor | | Peptide mimetic proteasome inhibitors for the treatment of cancer and inflammation. |
| proteasome inhibitors, Signature | peptide mimetics, Signature; proteasome inhibitors, Signature | Inflammatory disease, unspecified | Proteasome inhibitor | | |
| proteasome inhibitors, Takeda | proteasome inhibitors, Millenium; proteasome inhibitors, Takeda | Cancer, unspecified | Proteasome inhibitor | | A series of human 20S proteasome non-covalent inhibitors derived from N-β-neopentyl asparagine, for the treatment of cancer. |
| proteasome inhibitors, Telik | proteasome inhibitors, Telik | Cancer, unspecified | Proteasome inhibitor | | A mall-molecule, orally-active, non-peptide and non-boron-based proteasome inhibitors, for the treatment of cancer. |
| proteasome inhibitors, Novartis | proteasome inhibitors, Novartis | Cancer, unspecified | Proteasome inhibitor; Apoptosis stimulant | | |
| proteasome inihibitors, | proteasome inihibitors, | Cancer, hematological; | Proteasome Inhibitor | | |

TABLE 2-continued

Additional Proteasome Inhibitors

| Generic Name | Drug Name | Drug Disease | Mechanism of Action | Delivery Route | Notes |
|---|---|---|---|---|---|
| IkerChem syrbactins, Pono Pharma | IkerChem syrbactins, Pono Pharma | unspecified; solid Cancer, myeloma; unspecified | Proteasome inhibitor | | |
| timosaponin AIII | AA-101; AA102; AA-102; BN-108; timosaponin AIII | Cancer, breast | Apoptosis stimulant; Caspase stimulant; Proteasome inhibitor | Oral; Oral, swallowed | Oral plant-based aqueous extract from *Anemarrhena asphodeloides bunge*, which attenuates mitochondrial membrane potential to cause cytochrome C release and caspase activation, inducing low molecular grade apoptosis, which was under development for the treatment of breast cancer. It induces cancer cell death via activation of the AKT and mTOR pathways in breast cancer cells, but not normal cells. Phase II testing. |
| TMC-86A | proteasome inhibs, Tanabe; TMC-86A; TMC-86B; TMC-96 | Immunological disease, unspecified Inflammatory disease, unspecified | Proteasome inhibitor | | TMC-86A, TMC-86B and TMC-96 are 20S proteasome inhibitors with epoxy-β-aminoketone moieties, which were under investigation for the treatment of inflammatory disease, autoimmune diseases and muscle wasting associated with cancer cachexia, diabetes and sepsis. The compounds were isolated from *Streptomyces* sp TC-1084 and *Saccharothrix* |

TABLE 2-continued

Additional Proteasome Inhibitors

| Generic Name | Drug Name | Drug Disease | Mechanism of Action | Delivery Route | Notes |
|---|---|---|---|---|---|
| TMC-95A | TMC-95A; TMC-95B; TMC-95C; TMC-95D | Immunological disease, unspecified Inflammatory disease, unspecified Musculoskeletal disease, unspecified | Proteasome inhibitor | | sp TC-1094 (J Antibiot, 1999, 52, 1069). TMC-95A and its diastereomers, TMC-95B to D are 20S proteasome inhibitors, which were under investigation for the treatment of inflammatory and autoimmune diseases, and rapid muscle wasting associated with cancer cachexia, diabetes and sepsis. This series of cyclic peptides was isolated from *Apiospora montagnei Sacc*, TC-1093. |
| TQB-3602 | TQB 3602; TQB3602; TQB-3602 | Cancer, myeloma | Proteasome inhibitor | | TQB-3602 is a proteasome inhibitor, under development for the treatment of multiple myeloma. Phase I testing. |
| Ubiquitin Proteasome Program | ubiquitin proteasome system | Cancer | Proteasome inhibitor | | |
| VL-01 | 4SC-206, SC-68896, SC68896 | Hepatitis C (HCV); HIV (Antiviral) | Proteasome Inhibitor that induces apopotosis | | |
| VLX157 | VLX1570 | Cancer-bone, mantle cell lymphoma, multiple myeloma | Proteasome inhibitor | | |

All of the agents discussed herein can be in the form of pharmaceutical compositions.

Most preferred methods of administration of the agents and compositions for use in the disclosed methods are oral and parental including intravenous and injection. The pharmacological agent must be in the appropriate form for administration of choice.

Such pharmaceutical compositions comprising one or more pharmacological agents for administration may comprise a therapeutically effective amount of the pharmacological agent and a pharmaceutically acceptable carrier.

The phrase "pharmaceutically acceptable" as used herein refers to molecular entities and compositions that are physiologically tolerable and do not typically produce an allergic or similar untoward reaction, such as gastric upset, dizziness and the like, when administered to a human, and approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the therapeutic is administered. Such pharmaceutical carriers can be sterile liquids, such as saline solutions in water and oils, including those of petroleum, animal, vegetable, or synthetic origin, such as peanut oil, soybean oil, mineral oil, sesame oil, and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents.

Pharmaceutical compositions adapted for oral administration may be capsules, tablets, powders, granules, solutions, syrups, suspensions (in non-aqueous or aqueous liquids), or emulsions. Tablets or hard gelatin capsules may comprise lactose, starch or derivatives thereof, magnesium stearate, sodium saccharine, cellulose, magnesium carbonate, stearic acid or salts thereof. Soft gelatin capsules may comprise vegetable oils, waxes, fats, semi-solid, or liquid polyols. Solutions and syrups may comprise water, polyols, and sugars. An active agent intended for oral administration may be coated with or admixed with a material that delays disintegration and/or absorption of the active agent in the gastrointestinal tract. Thus, the sustained release may be achieved over many hours and if necessary, the active agent can be protected from degradation within the stomach. Pharmaceutical compositions for oral administration may be formulated to facilitate release of an active agent at a particular gastrointestinal location due to specific pH or enzymatic conditions.

A further preferred form of administration is parenteral including intravenous administration. Pharmaceutical compositions adapted for parenteral administration, including intravenous administration, include aqueous and non-aqueous sterile injectable solutions or suspensions, which may contain anti-oxidants, buffers, bacteriostats, and solutes that render the compositions substantially isotonic with the blood of the subject. Other components which may be present in such compositions include water, alcohols, polyols, glycerine, and vegetable oils. Compositions adapted for parental administration may be presented in unit-dose or multi-dose containers, such as sealed ampules and vials, and may be stored in a freeze-dried (lyophilized) condition requiring only the addition of a sterile carrier, immediately prior to use. Extemporaneous injection solutions and suspensions may be prepared from sterile powders, granules, and tablets. Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

Pharmaceutical compositions adapted for nasal and pulmonary administration may comprise solid carriers such as powders, which can be administered by rapid inhalation through the nose. Compositions for nasal administration may comprise liquid carriers, such as sprays or drops. Alternatively, inhalation directly through into the lungs may be accomplished by inhalation deeply or installation through a mouthpiece. These compositions may comprise aqueous or oil solutions of the active ingredient. Compositions for inhalation may be supplied in specially adapted devices including, but not limited to, pressurized aerosols, nebulizers or insufflators, which can be constructed so as to provide predetermined dosages of the active ingredient.

Further methods of administration include sublingual, vaginal, buccal, rectal, or transdermal administration to a subject.

In some instances, the agent is in a next generation formulation such as nanoencapsulation, such as bortezomib. Such formulations are under investigation for cancer treatment.

Selection of a therapeutically effective dose will be determined by the skilled artisan considering several factors, which will be known to one of ordinary skill in the art. Such factors include the particular form of the pharmacological agent, and its pharmacokinetic parameters such as bioavailability, metabolism, and half-life, which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether the administration is acute or chronic, concomitant medications, and other factors well known to affect the efficacy of administered pharmaceutical agents. Thus, the precise dose should be decided according to the judgment of the person of skill in the art, and each patient's circumstances, and according to standard clinical techniques.

Doses can be adjusted to optimize the effects in the subject. For example, the agent can be administered at a low dose to start and then increased over time to depending upon the subject's response. A subject can be monitored for improvement of their condition prior to changing, i.e., increasing or decreasing, the dosage. A subject can also be monitored for adverse effects prior to changing the dosage, i.e., increasing or decreasing, the dosage.

The FDA approved PIs and dosages are found in Table 1. It will be appreciated by those of skill in the art that the subjects on which the methods of the present disclosure are being practiced are under 10 years of age and in some cases under one year of age. Thus, the therapeutically effective dosages for these subjects may be less than the FDA approved dosages.

The agents may be administered daily, weekly, biweekly, several times daily, semi-weekly, every other day, bi-weekly, quarterly, several times per week, semi-weekly, monthly, or more. The duration and frequency of treatment may depend upon the subject's response to treatment.

The agents described herein can be co-administered with other agents including those disclosed herein and additional ones for the prevention and treatment of vascular malformations. The co-administration of agents can be by any administration described herein. Moreover, it can be in one composition, or in more than one composition. The administration of the agents can be simultaneous, concurrently or sequentially.

Treatment using the present methods can continue as long as needed.

Kits

Also within the scope of the present disclosure are kits for practicing the disclosed methods.

In some embodiments, the kit can comprise instructions for use in any of the methods described herein. The included instructions can comprise a description of administration of the agents to a subject to achieve the intended activity in a subject. The kit may further comprise a description of selecting a subject suitable for treatment based on identifying whether the subject is in need of the treatment.

The instructions relating to the use of the agents described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the pharmaceutical compositions are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device, such as an inhaler, nasal administration device, or an infusion device. A kit may have a sterile access port (for example, the container may be an intravenous solution bag or a vial having a stopper pierceable by a hypodermic injection needle). The container may also have a sterile access port.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

EXAMPLES

The present invention may be better understood by reference to the following non-limiting examples, which are presented in order to more fully illustrate the preferred embodiments of the invention. They should in no way be construed to limit the broad scope of the invention.

Example 1—Direct Targeting of Affected Pathways with Known Drugs

LMECs and matching tissue with an activating mutation in PIK3CA or an inactivating mutation in RASA1 had increased AKT and ERK activation when compared to control tissue and cells, respectively. LMECs carry inactivating mutations in PIK3R3/TSC2 unexpectedly displayed increased ERK activation as well as AKT activation. Using these cells, it was earlier found that the LMECs with MAPK pathway activation were resistant to sirolimus, a mTOR inhibitor commonly used to treat LMs. See FIG. 1A.

It was then asked whether this finding was specific to sirolimus, or to inhibitors that target the PI3K/AKT/MTOR pathway. The effect of inhibiting the MAPK (RAS/MAPK) pathway on proliferation of these cells was also assessed.

Cells with the same mutations (Pik3ca, Pik3r3/Tsc2, Rasa1; LMEC8, LMEC28, and LMEC10 respectively), (Table 3) were treated with increasing log doses of alpelisib, a PI3K inhibitor, ranging from 1 μM to 100 μM. Proliferation rate was determined by WST-8 assay and expressed as a fraction of the number of cells in vehicle controls.

It was found that alpelisib significantly inhibited both control and the LMECs at concentrations flanking the calculated human sera level of 75 μM; it was more effective than sirolimus. However, at lower doses, LMEC responses were different.

Cells with only PIK3CA mutation (and only increased AKT signaling) were more sensitive to alpelisib, while the cells with increased ERK signaling were more resistant when compared to control HDLECs (FIG. 1B). These results were similar to sirolimus (FIG. 1A).

Figure 1C:
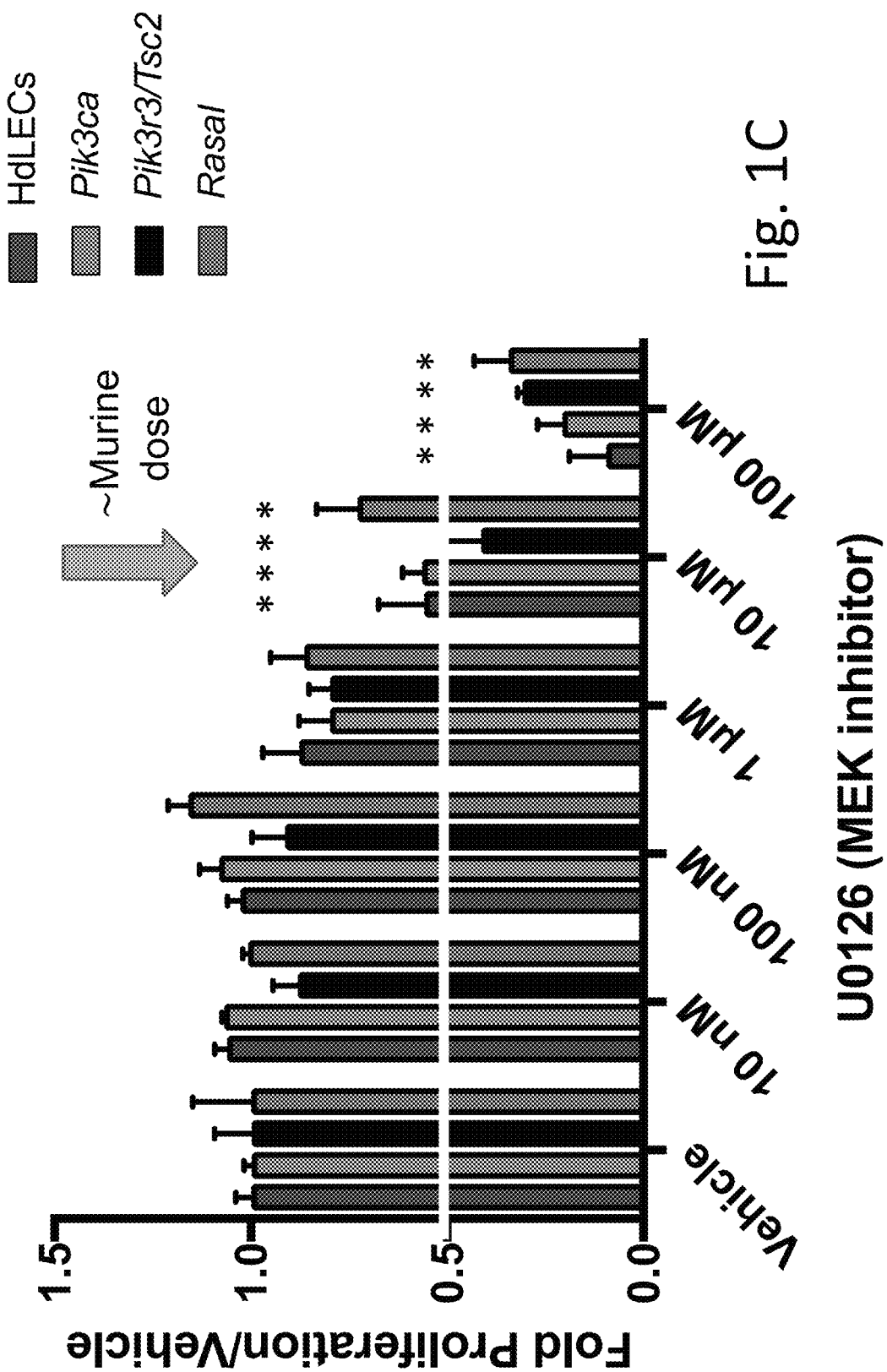
FIG. 1C shows results of the same cells treated with increasing log doses of the MAPK kinase inhibitor U0126. Proliferation rate was determined by WST-8 assay and expressed as a fraction of the number of cells in vehicle controls±SD. *$p<0.05$. The large arrow denotes the range of human doses (FIGS. 1A and 1B) and murine doses (FIG. 1C) used in clinical setting.

Cells were also treated with U0126, a MAPK inhibitor, in increasing log doses ranging from 1 μM to 100 μM. At the concentration used in animal models (10 μM), U0126 suppressed the growth of all cells by 50% (FIG. 1C).

Interestingly, cells with the RASA1 mutations were not any more sensitive to MAPK inhibition than those with the PIK3CA mutation or control cells. These data demonstrated that drug responses were affected by genetic variants, and MAPK hyperactivation may contribute to pathogenic proliferation of LMECs.

Example 2—Unbiased High Throughput Screening (HTS) of ECs Identified Omipalisib and Proteasome Inhibitors as Effective ECs from vascular malformation tissues carrying known disease associated pathogenic variants, including those that target the PI3K/AKT/mTOR and RAS/RAF/MAPK pathways have been collected. It was hypothesized that ECs isolated from patients that carried pathogenic somatic, as well as yet to be identified variants, could be used in a drug screen to identify novel therapies for the treatment of vascular malformations.

High throughput screening of drugs was performed using ECs from either LMs (LMECs) or VM (VMECs) carrying pathogenic variants in genes of the PI3K/AKT/mTOR pathway or variants predicted to hyperactivate the RAS/RAF/MAPK pathway (Table 3).

Per optimization studies, about 500 cells were seeded into the wells of a 384-well plate and the VMECs or LMECs were treated with 1 μM of approximately 2500 drugs, which were either in clinical trials or FDA approved for another condition. The effects of the drugs on the proliferation and cell viability of the cells were assessed. Cell viability relative to vehicle treated cells was determined after 48 hours.

Figure 3:
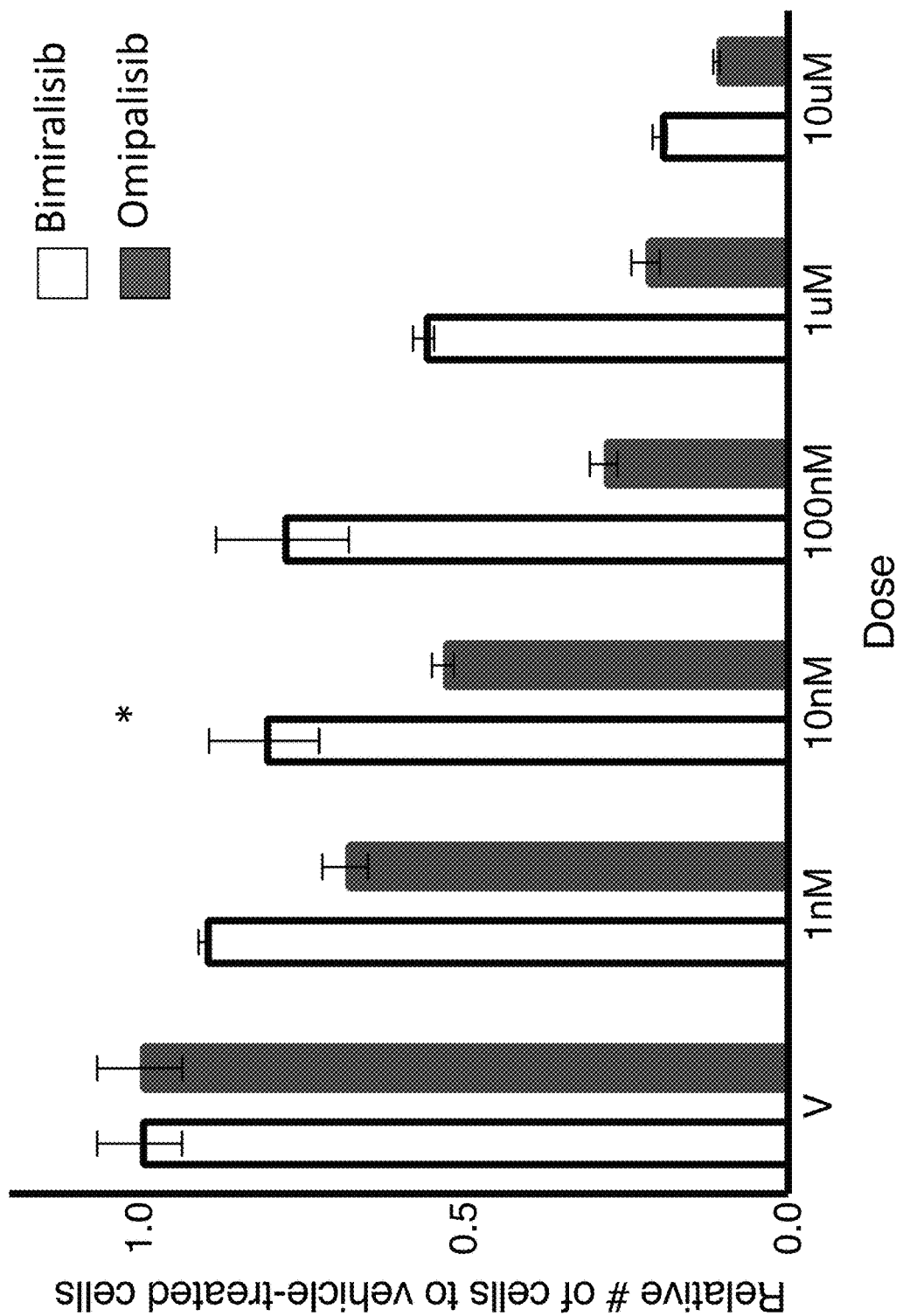
FIG. 3—Omipalisib demonstrated as a specific inhibitor with improved efficacy against LMEC28. Cell survival was determined after 48 hours and data presented as percent cell survival of cells treated versus vehicle treated cells. Omipalisib, a PI3K/mTOR inhibitor, at a lower dose (*) was more efficacious than another PI3K/mTOR dual inhibitor, bimiralisib, in inhibiting LMEC proliferation. At 10 nM; TTEST $p<0.03$.

HTPS identified several candidate drugs that inhibited the PI3K/AKT signaling pathways (FIG. 2). Interestingly, the inhibitory effects on of the same class of drugs on all VMEC and LMEC proliferation were variable across all cell populations. As an example, omipalisib, a dual PI3K/mTOR inhibitor, was more efficacious in inhibiting vascular malformation cells than voxtalisib, another PI3K/mTOR dual inhibitor. As omipalisib was found as the strongest PI3K/mTOR dual inhibitor of LMEC and VMEC proliferation in the HTPS screen, another dual PI3K/mTOR inhibitor, bimiralisib, was assessed as it was not in the HTPS panel (FIG. 3). Omipalisib was significantly more efficacious than bimiralisib at every dose in inhibiting an LMEC population, suggesting omipalisib may be the optimal drug in its class to target the pathological growth in LMs and VMs.

Figure 4:
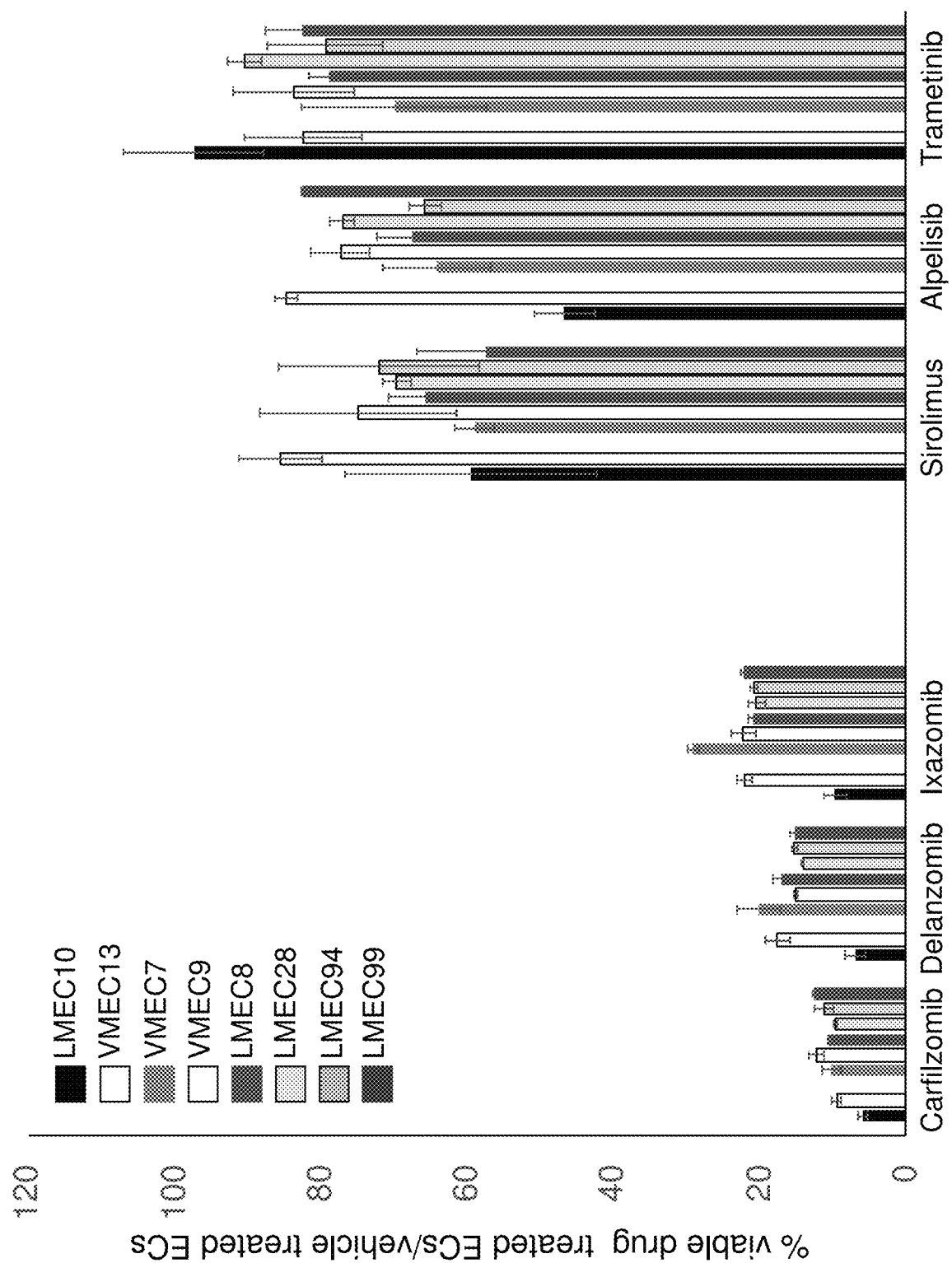
FIG. 4—Proteasome Inhibitors efficaciously suppressed VMEC and LMEC growth/viability more than that observed for drugs used off label for vascular malformation patients.

A novel class of therapeutics, proteasome inhibitors (PIs), were identified in the HTPS that were more efficacious at suppressing cell growth/viability than drug therapies currently used off-label for VM and LM patients, sirolimus and alpelisib (FIG. 4; Table 4). The 3 PIs tested in the HTPS suppressed LMEC (n=5) and VMEC (n=3) cell numbers 75%-90% relative to vehicle treated cells, while sirolimus and alpelisib reduced their growth and viability only 40-50%. The PIs had a much stronger effect on the LMECs and VMECs regardless of the mutation. As can be seen in Table 4, the 3 PIs tested in the HTPS were: number 1 in effectiveness for all cell variants (carfilzomib); number 2 for ⅝ cell variants and number 3 and 4 for the ⅜ (defanzomib);

and in the top 9 for all cell variants (ixazomib). In contrast, sirolimus and alpelisib ranged from number 28-383 for effectiveness for all variants.

TABLE 3

LMECs and VMECs Used in HTPS Screening

| Cell Population | Pathogenic Variant |
|---|---|
| LMEC8 | Pik3ca c.1636 C > A |
| LMEC10 | Rasa$^{frameshift}$c.617_621delTAAGA |
| LMEC28 | Pik3r3$^{Sp-Donor}$ 1:46527598 T/TA; Tsc2$^{5'utr}$ 16-2110805-G-A |
| LMEC94 | Pik3ca c.3140A > G |
| LMEC99 | Pik3ca c.1258T > C |
| VMEC7 | Pik3ca c.1035T > A |
| VMEC9 | Pik3ca c.1624G > A |
| VMEC13 | Map2k2c.1112g > A; Glmn$^{Sp-Donor}$c.1214+2T > C |

TABLE 4

Ranking of Proteasome Inhibitors in HTPS for Suppressing Cell Proliferation and Growth Compared to Drugs used for Off-Label Treatment

| Cell Pop. | Carfitzomib | Delanzomib | Ixazomib | Disulfiram | Sirolimus | Alpelisib | Trematinib |
|---|---|---|---|---|---|---|---|
| VMEC 13 | 1 | 2 | 8 | 8 | 118 | 107 | 79 |
| LMEC 10 | 1 | 3 | 5 | 3 | 383 | 50 | 1225 |
| VMEC 7 | 1 | 4 | 7 | 10 | 32 | 44 | 71 |
| VMEC 9 | 1 | 2 | 9 | 5 | 52 | 58 | 71 |
| LMEC 8 | 1 | 3 | 8 | 7 | 38 | 42 | 72 |
| LMEC 28 | 1 | 2 | 9 | 19 | 63 | 81 | 241 |
| LMEC 94 | 1 | 2 | 6 | 11 | 45 | 28 | 62 |
| LMEC 99 | 1 | 2 | 4 | 8 | 40 | 83 | 82 |

Example 3—Dose Response Studies of Proteasome Inhibitors and Omipalisib

Figures 5, 5A:
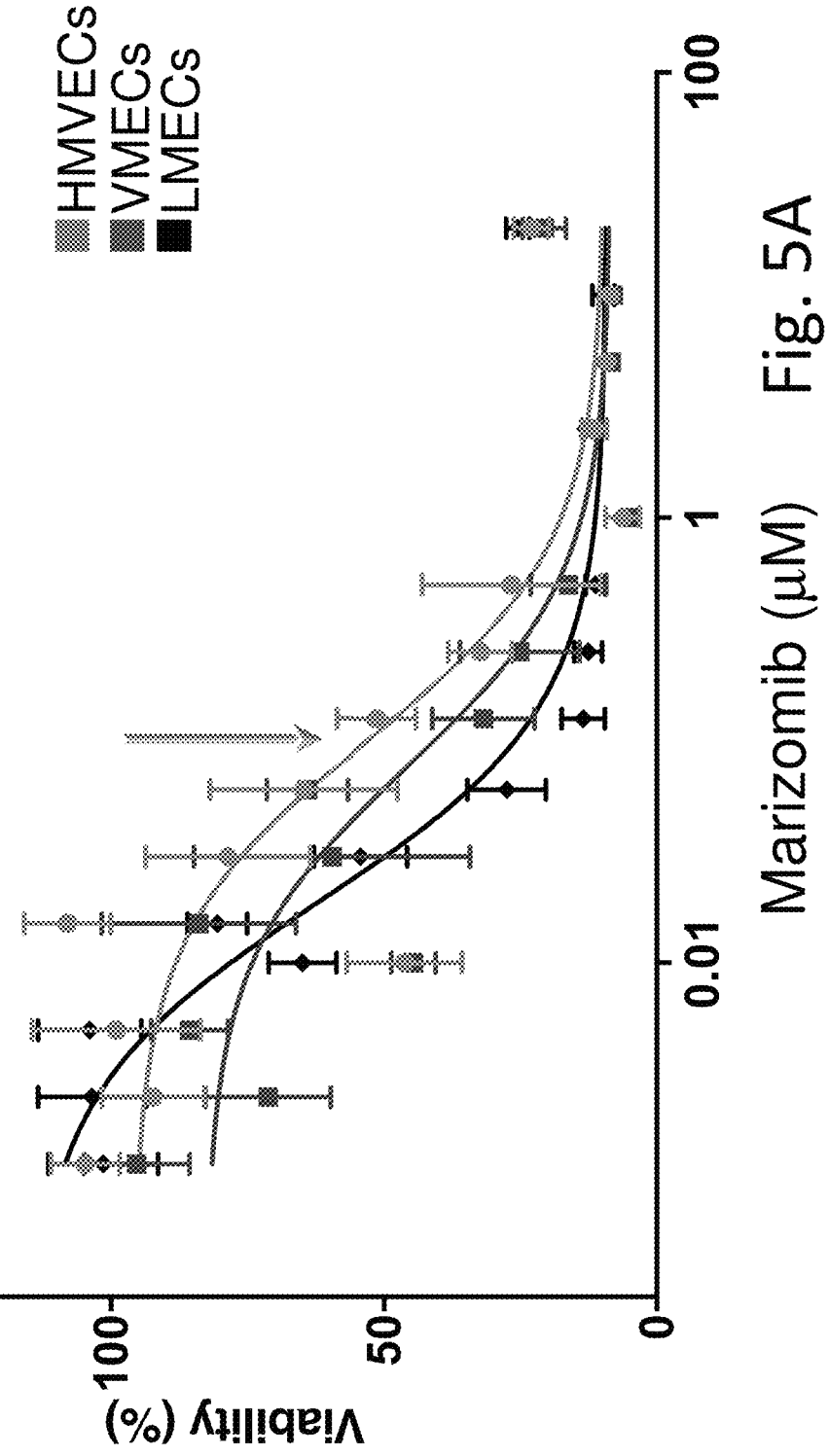
Figure 5B:
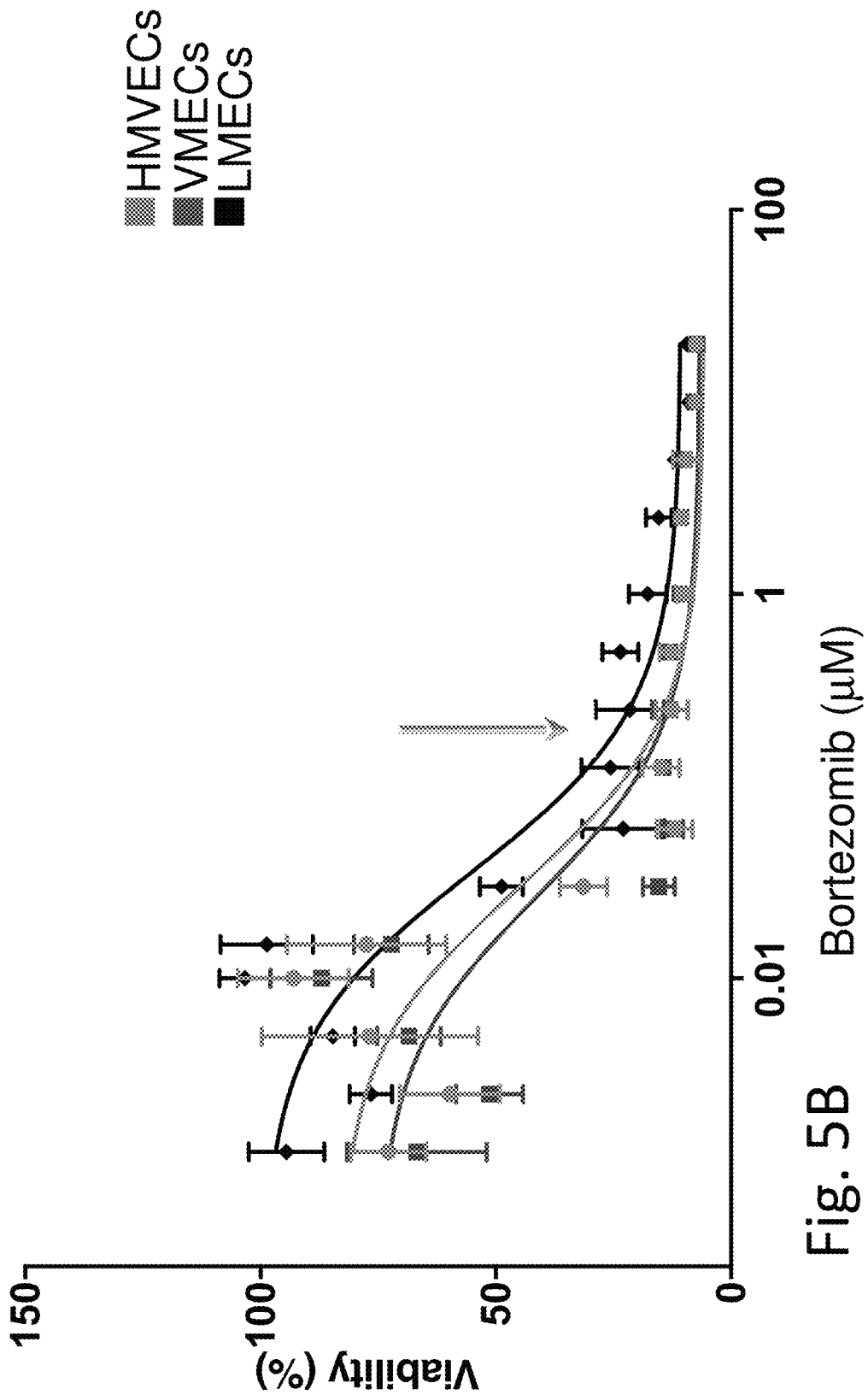
FIG. 5B shows bortezomib.
Figure 5C:
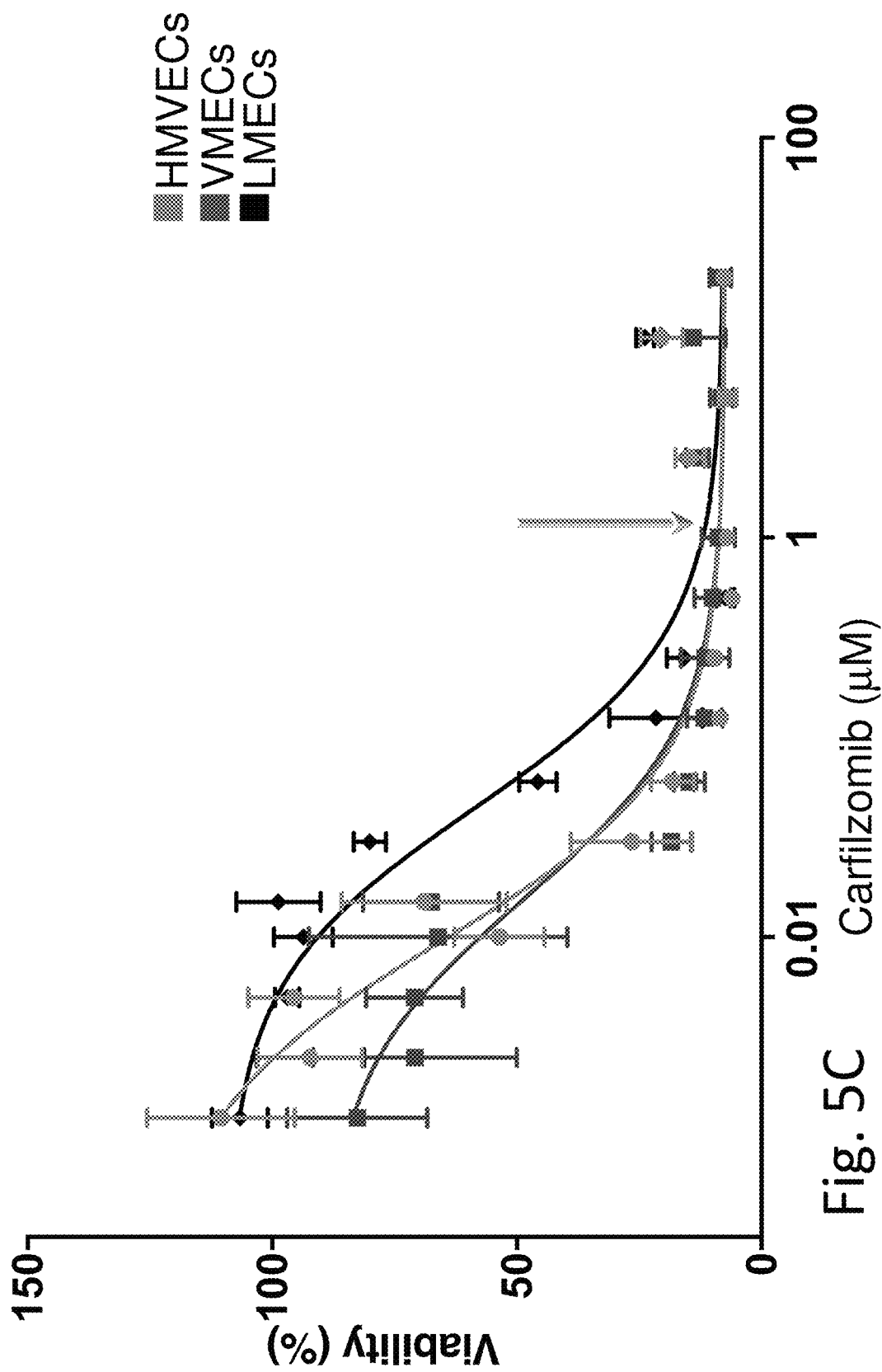
FIG. 5C shows carfilzomib.
Figure 5D:
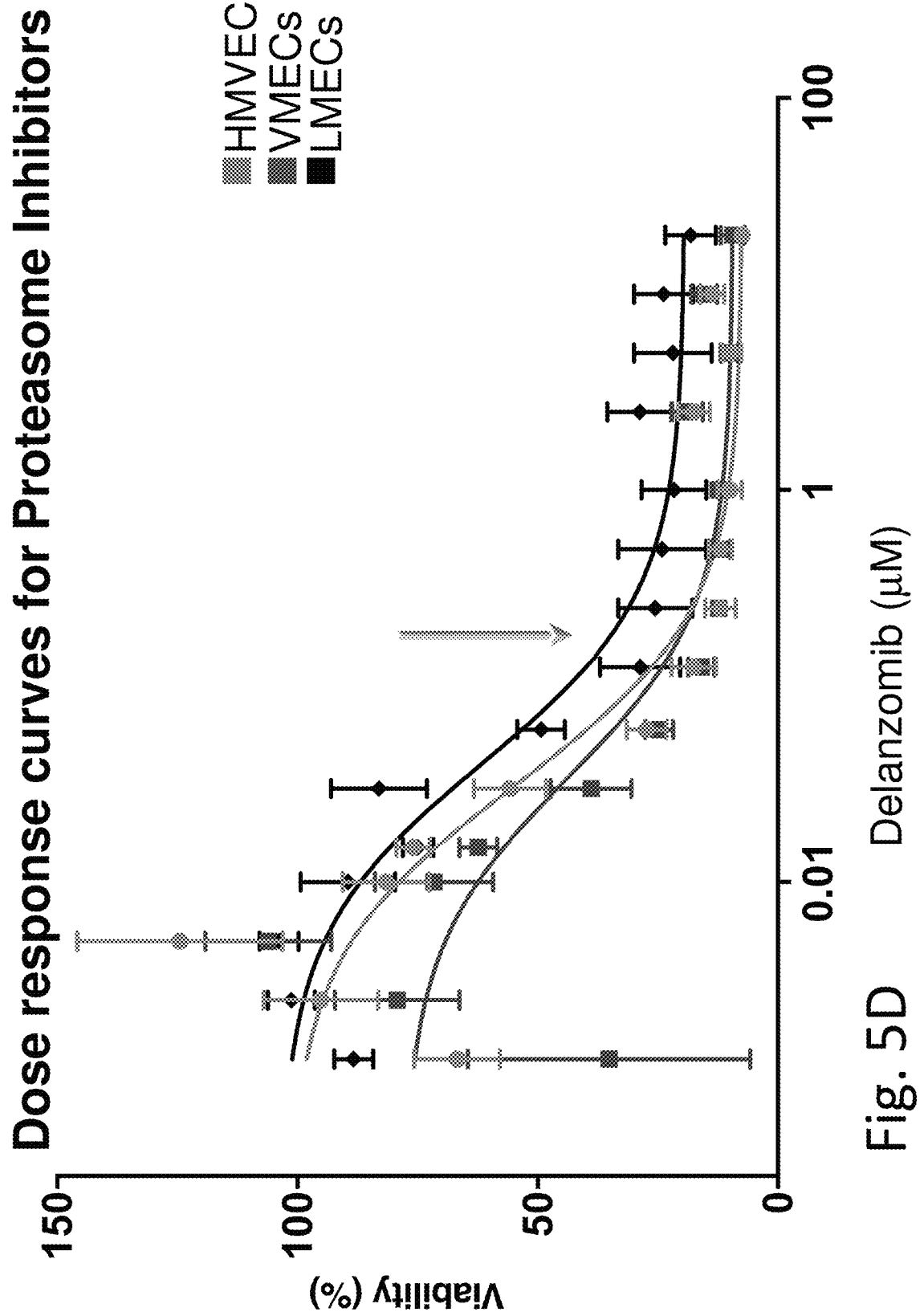
FIG. 5D show delanzomib.
Figure 5E:
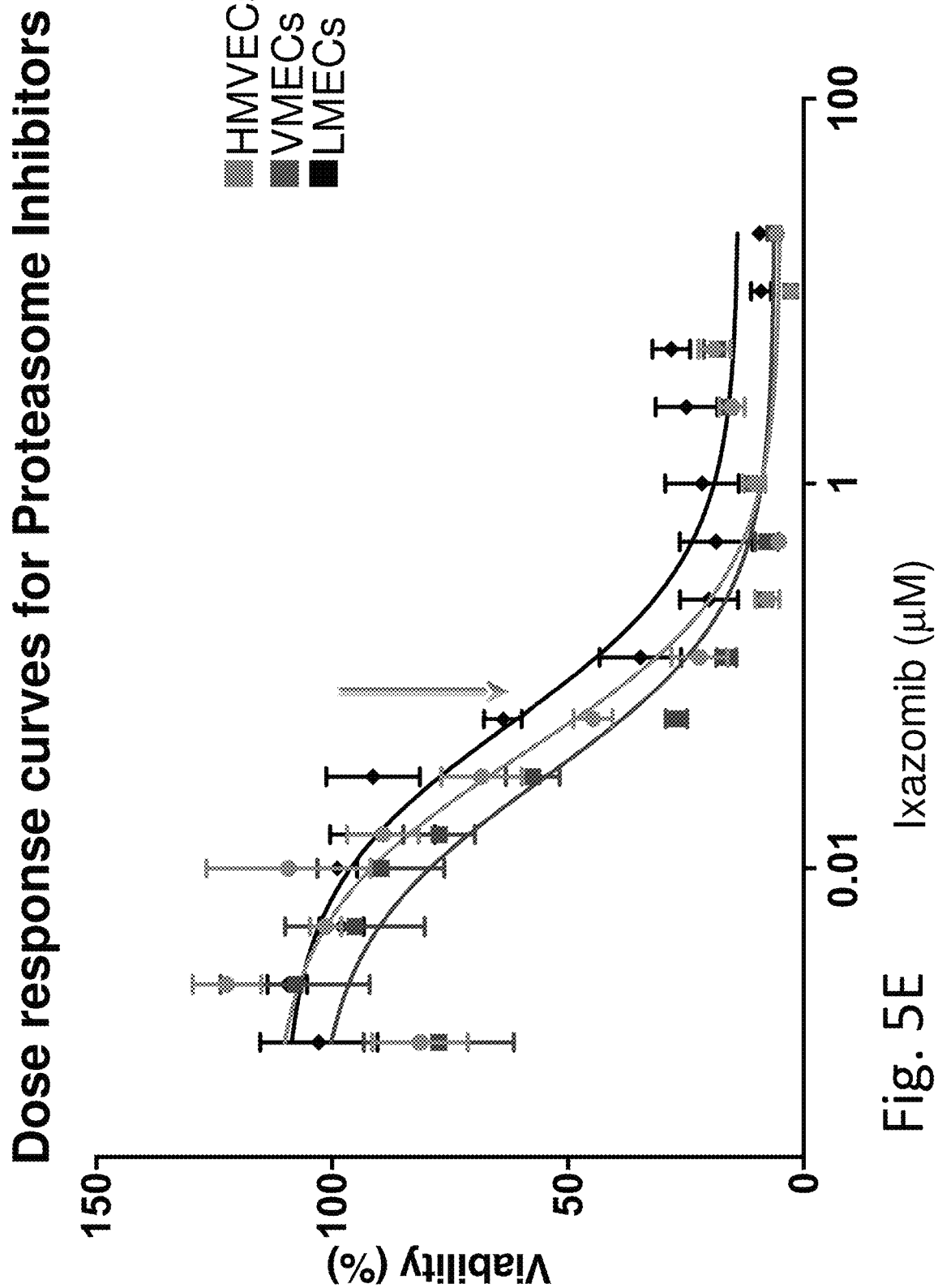
FIG. 5E shows ixazomib.
Figure 5F:
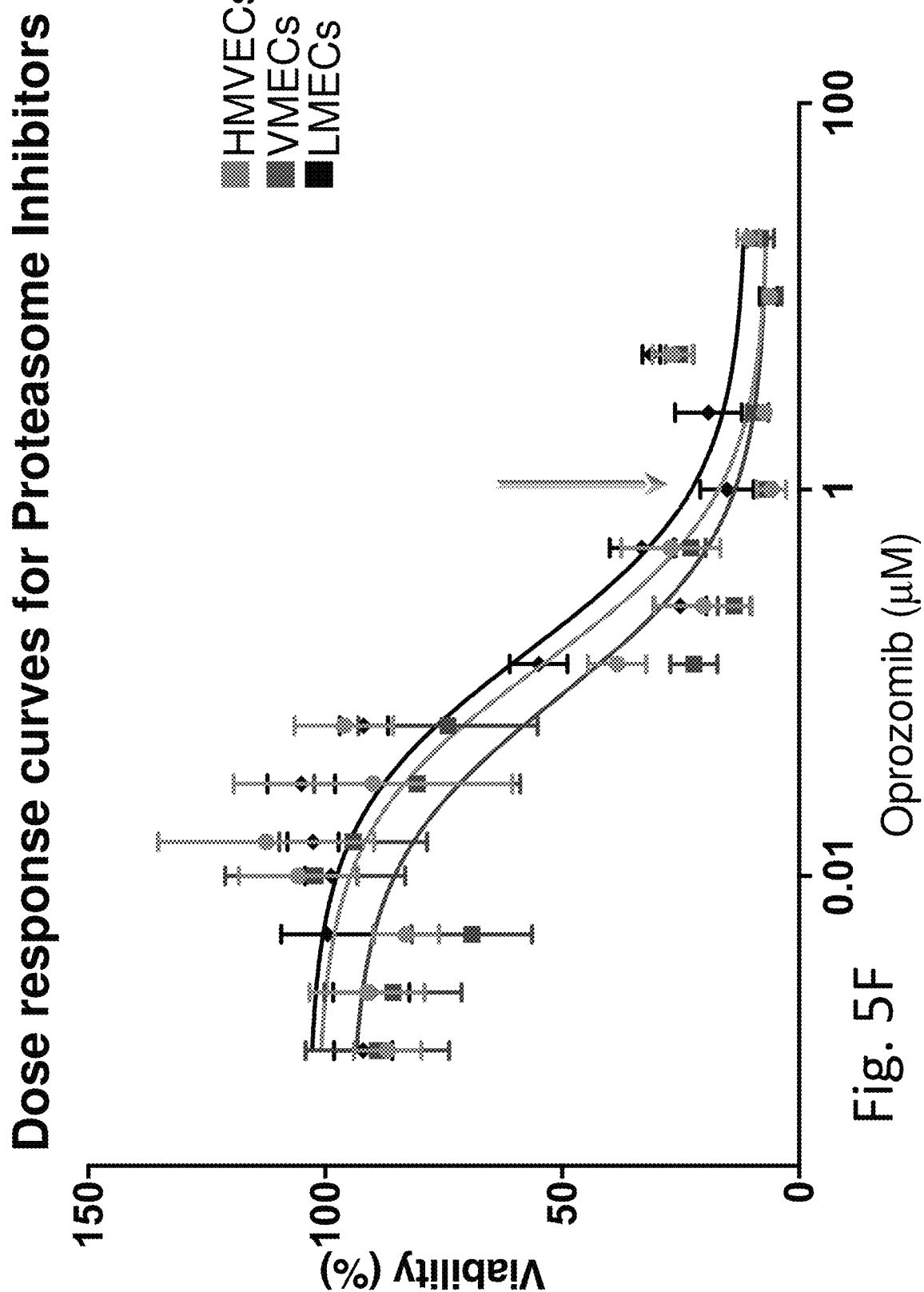
FIG. 5F shows oprozomib.
Figure 5G:
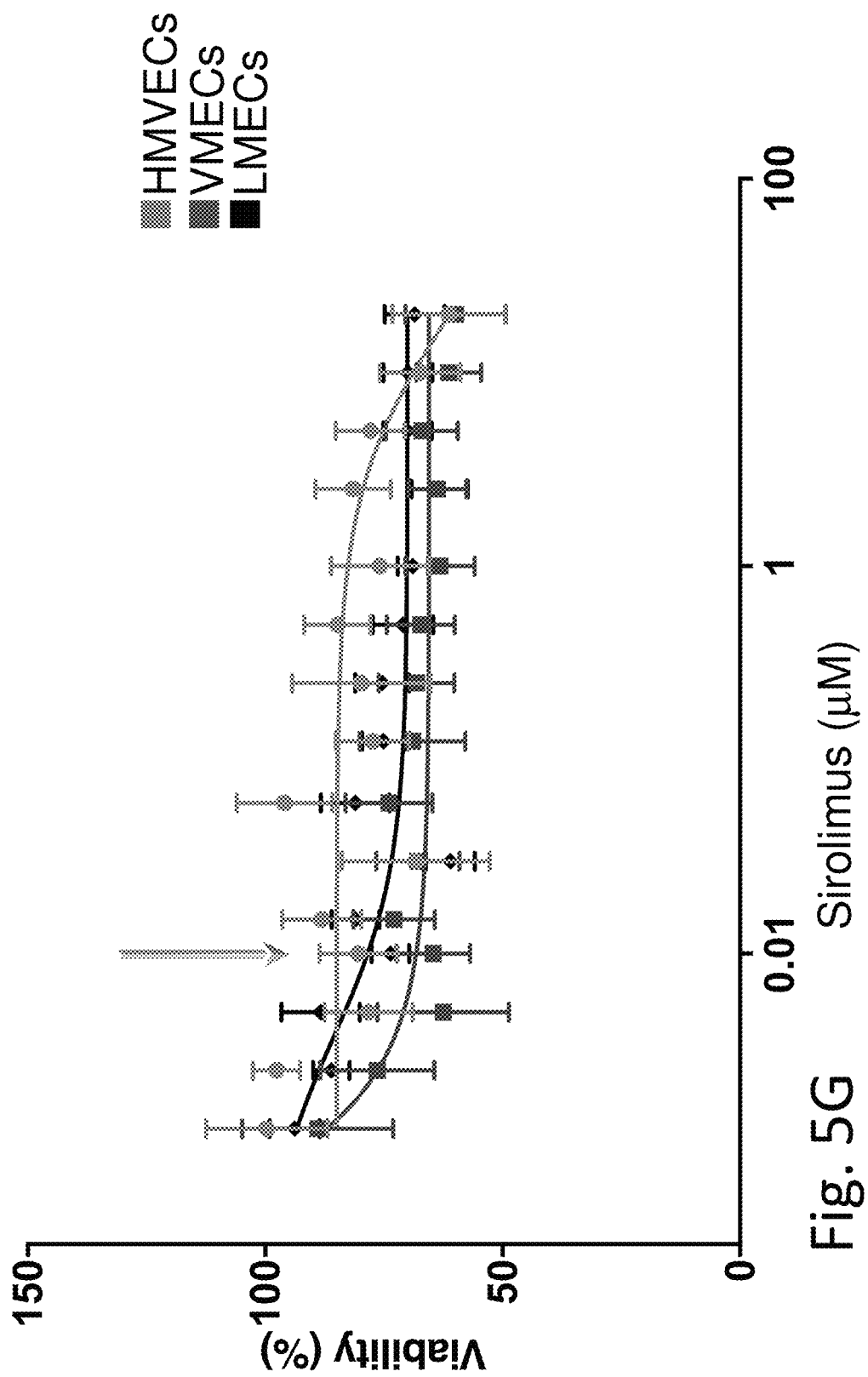
FIG. 5G shows sirolimus.
Figure 5H:
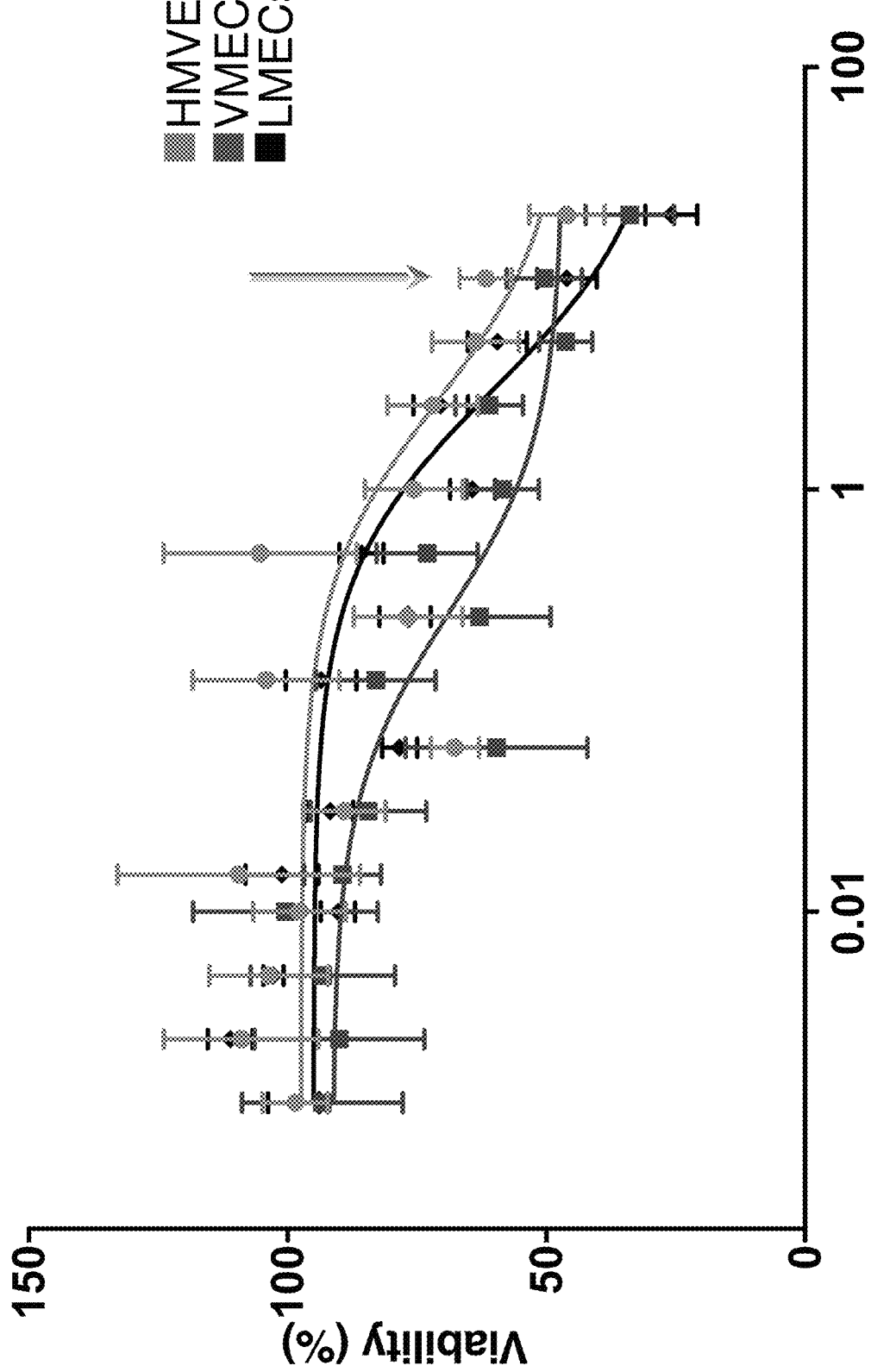
FIG. 5H shows alpelisib.
Figure 5I:
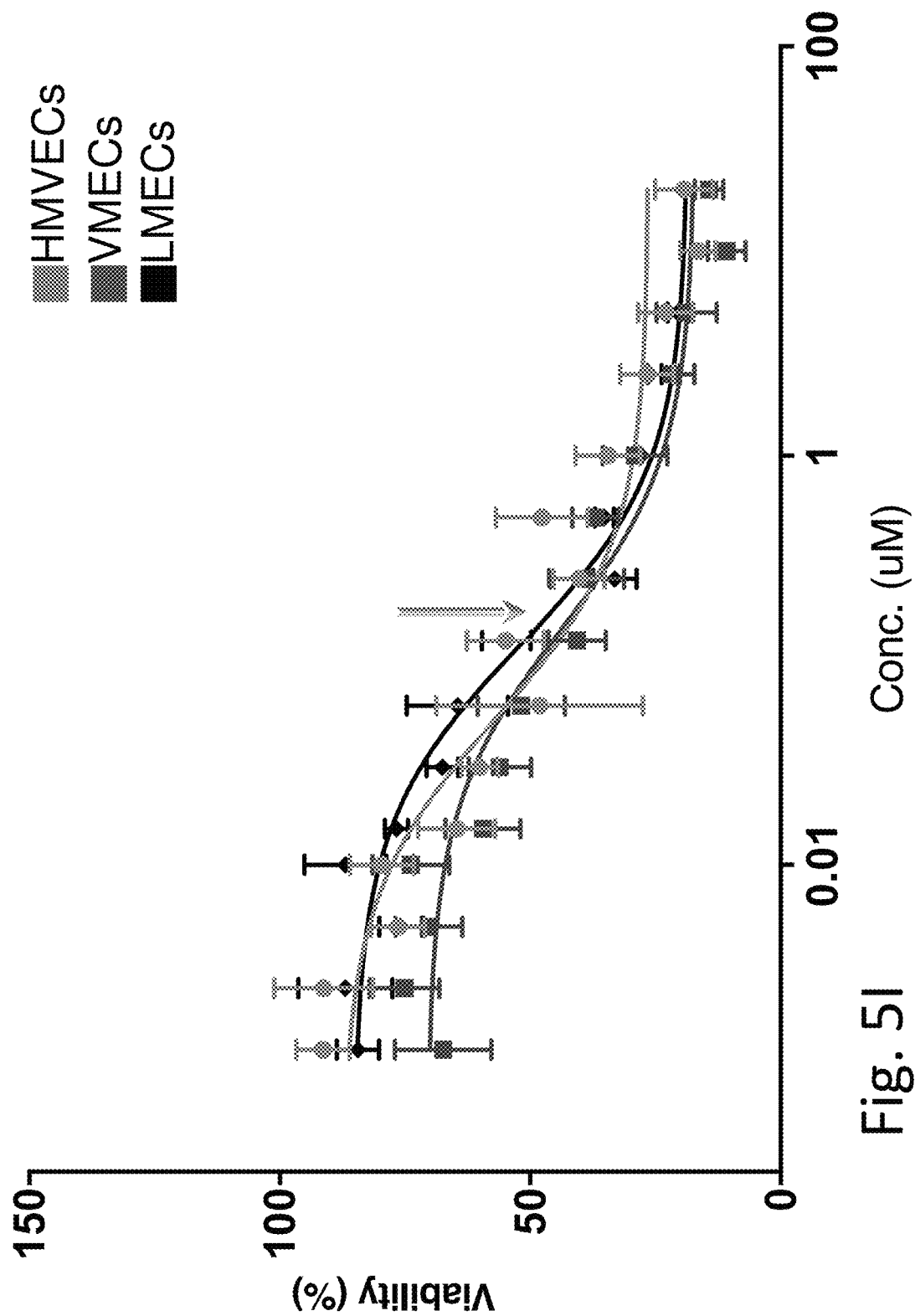
FIG. 5I shows omipalisib.
Figure 6:
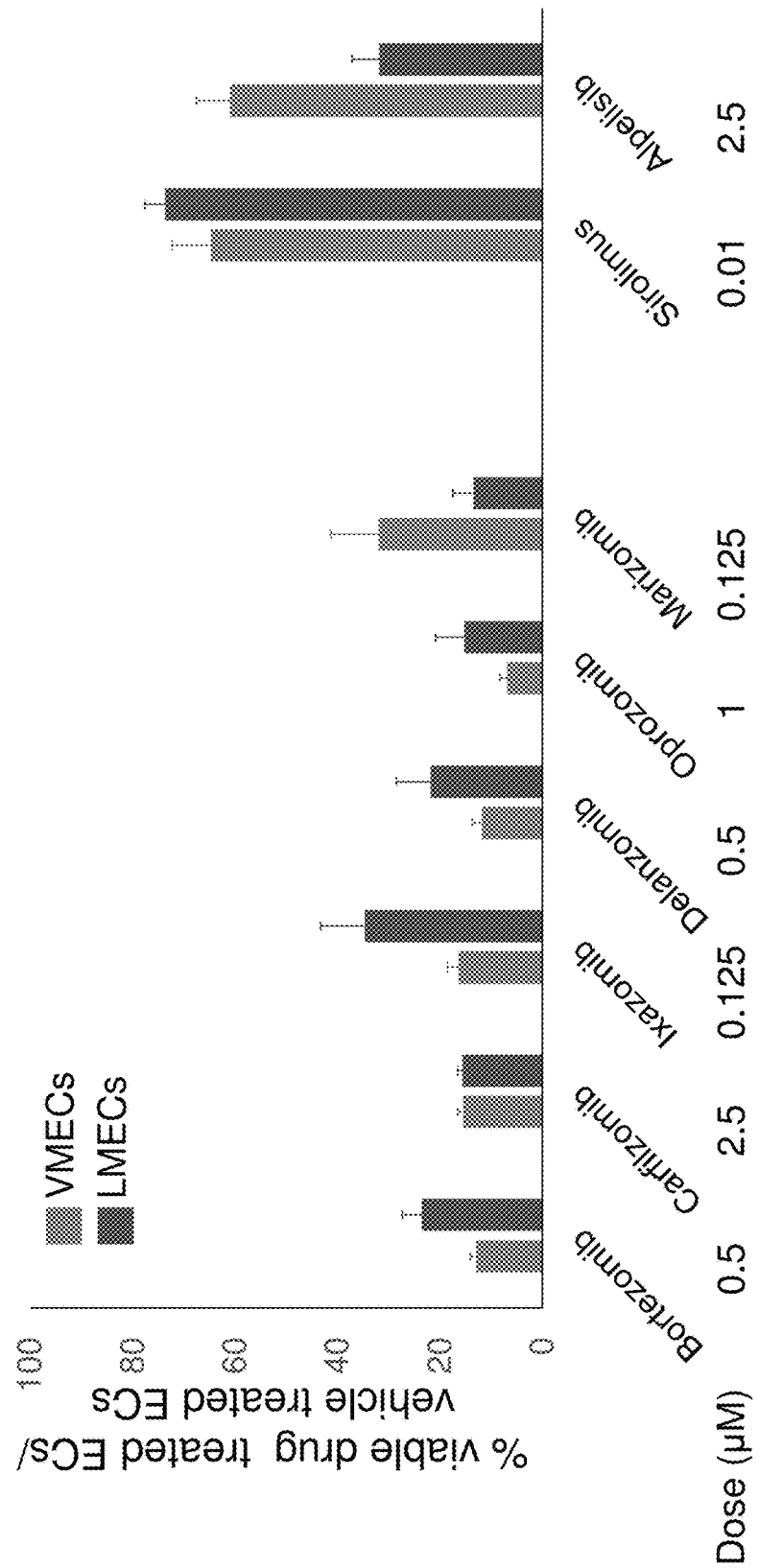
FIG. 6—Proteasome inhibitors (PIs) are more effective at reducing viable cells than current therapies currently used off-label for vascular malformation patients.

Using the plasma concentrations reported in the literature for six commercially available PIs (Table 1) and omipalisib (Lukey et al. 2019), a dose response study was performed using VMEC7, VMEC9, LMEC94 and LMEC99, all carrying Pik3ca variants (Table 3) as well as HMVECs. Cell growth and viability was measured as in Example 2 after 48 hours. The 6 PIs and omipalisib were all more effective at suppressing growth/viability of LMEC and VMEC carrying Pik3ca variants, than either sirolimus or alpelisib at clinically relevant doses (as shown by the arrows in FIG. 5) (FIGS. 5 and 6).

Example 4—Effectiveness of Proteasome Inhibitors is not Limited to VM/LM ECs with Pik3ca Variants LMEC28 cells which carries the Pik3r3;Tsc2 mutations were subjected to increasing amounts of oprozomib from 1 nM to 1 μM and cell viability determined after 48 hours as set forth in Example 2.

Figure 7:
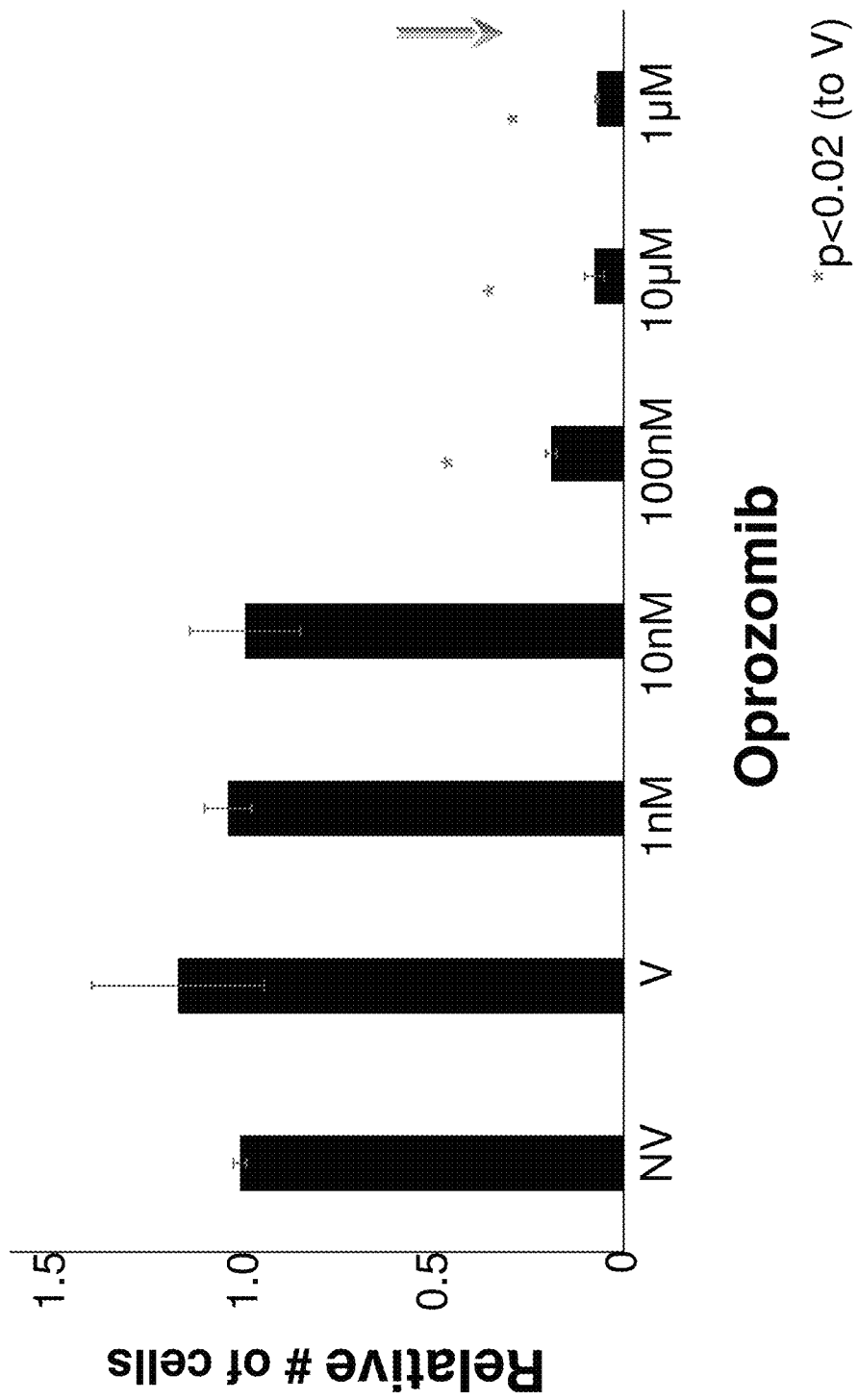
FIG. 7—PI effect not limited to VM/LM ECs with Pik3ca variants.

As shown in FIG. 7, there was a dose dependent inhibition of the LMECs carrying the Pik3r3; Tsc2 showing that the PI was effective in suppressing cell proliferation in cells harboring mutations other than Pik3ca.

Example 5—In Vivo Effectiveness of Proteasome Inhibitors on Treating VMs

To assess the efficacy of PIs in an animal, the effect of oprozomib was assessed in a xenograft model. VMECs carrying Pik3ca variants (n=2 VMECs; VMEC7 and VMEC9—Table 3; 4 implants each for treated and vehicle) were resuspended in Matrigel® (Corning) and subcutaneously implanted in the flanks of immunocompromised mice. VM vessels were allowed to develop and mice randomized for one week. After 1 week, mice were given either 30 mg/kg oprozomib or vehicle orally two days a week for 4 weeks. Oprozomib, a second generation of carfilzomib, was chosen as it is reported to be more tolerable, and orally available (Teicher and Tomaszewski 2017). After 4 weeks of treatment, mice were sacrificed, and the implants surgically removed. The vehicle-treated implant was vascular and easily distinguished from surrounding soft tissues. The oprozomib-treated implant had no vascularity on gross inspection. The outline of the Matrigel® was visualized as a translucent, oval-shaped foreign body in the subcutaneous space. The implants were then fixed by formalin, paraffin embedded for histological analysis. Five (5) micron sections were stained with Hematoxylin and Eosin and images captured and used to assess implant morphology and vascularity.

Figure 8B:
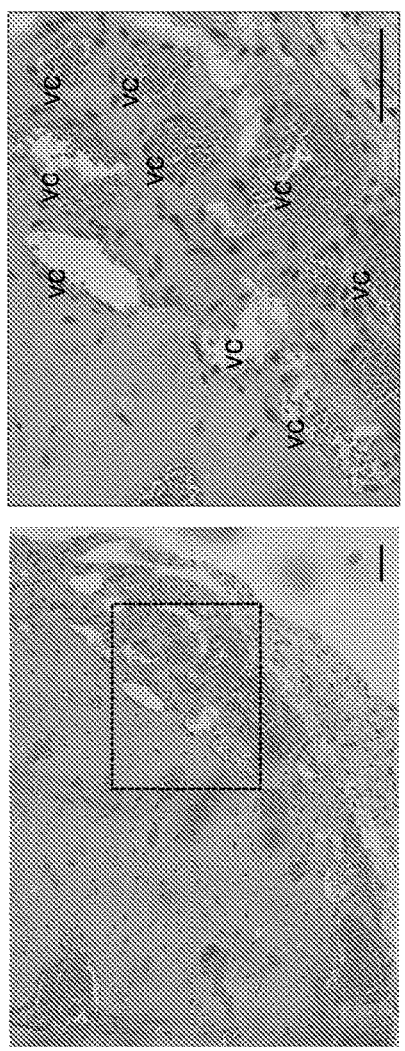
FIG. 8B are representative H&E images of vehicle and oprozomib treated implants. Boxed area is enlarged to the right. Scale bar—50 μm.
Figure 8A:
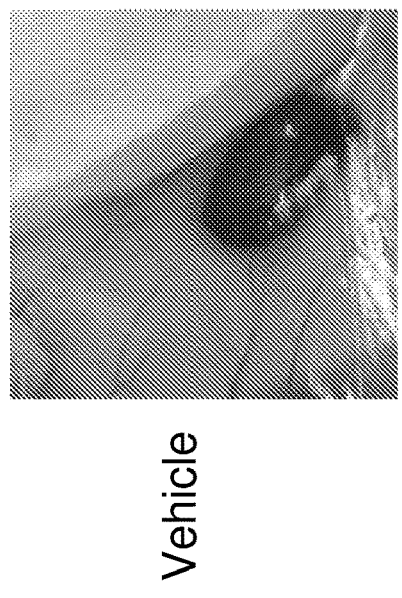
FIG. 8A are images of the gross appearance of implants after treatment with vehicle or oprozomib. The dotted line marks the border of the Matrigel®.
Figure 8C:
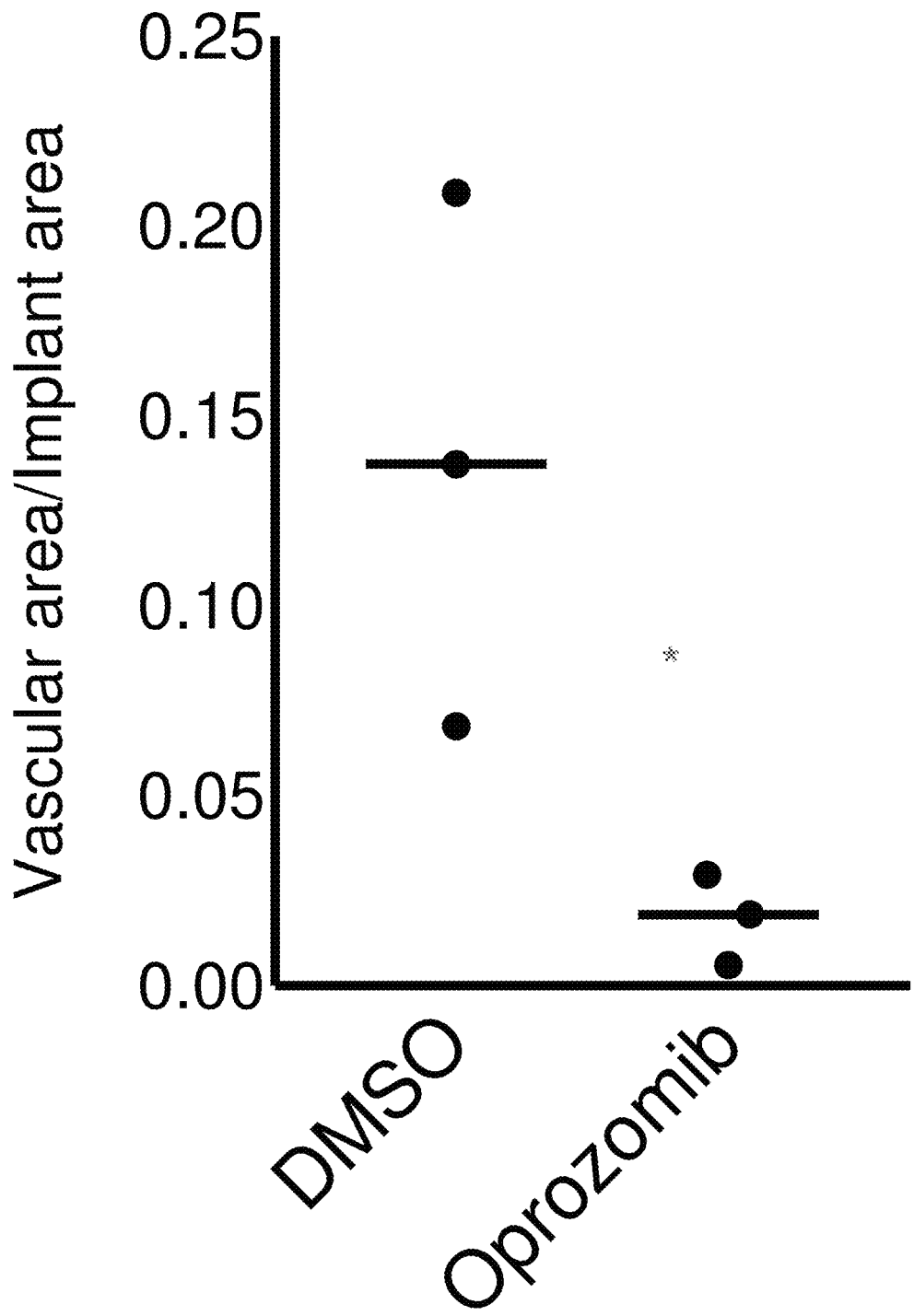
FIG. 8C is a graph of the quantification of vascular area normalized to area. *p<0.05. vc—vascular channels.

Findings were dramatic. The implants in the vehicle treated group were highly vascularized and hemorrhagic. In contrast, the vessels appeared to be regressed or normalized in the implants from the treatment group. See FIG. 8. Additionally, no adverse effects were seen in the treated mice.

Taken together, these results demonstrate that PIs are efficacious against pathological VMECs and LMECs carrying genetic variants in the two most commonly mutated pathways in vascular malformations, PI3K/AKT/mTOR and RAS/RAF/MAPK pathways.

Figure 9:
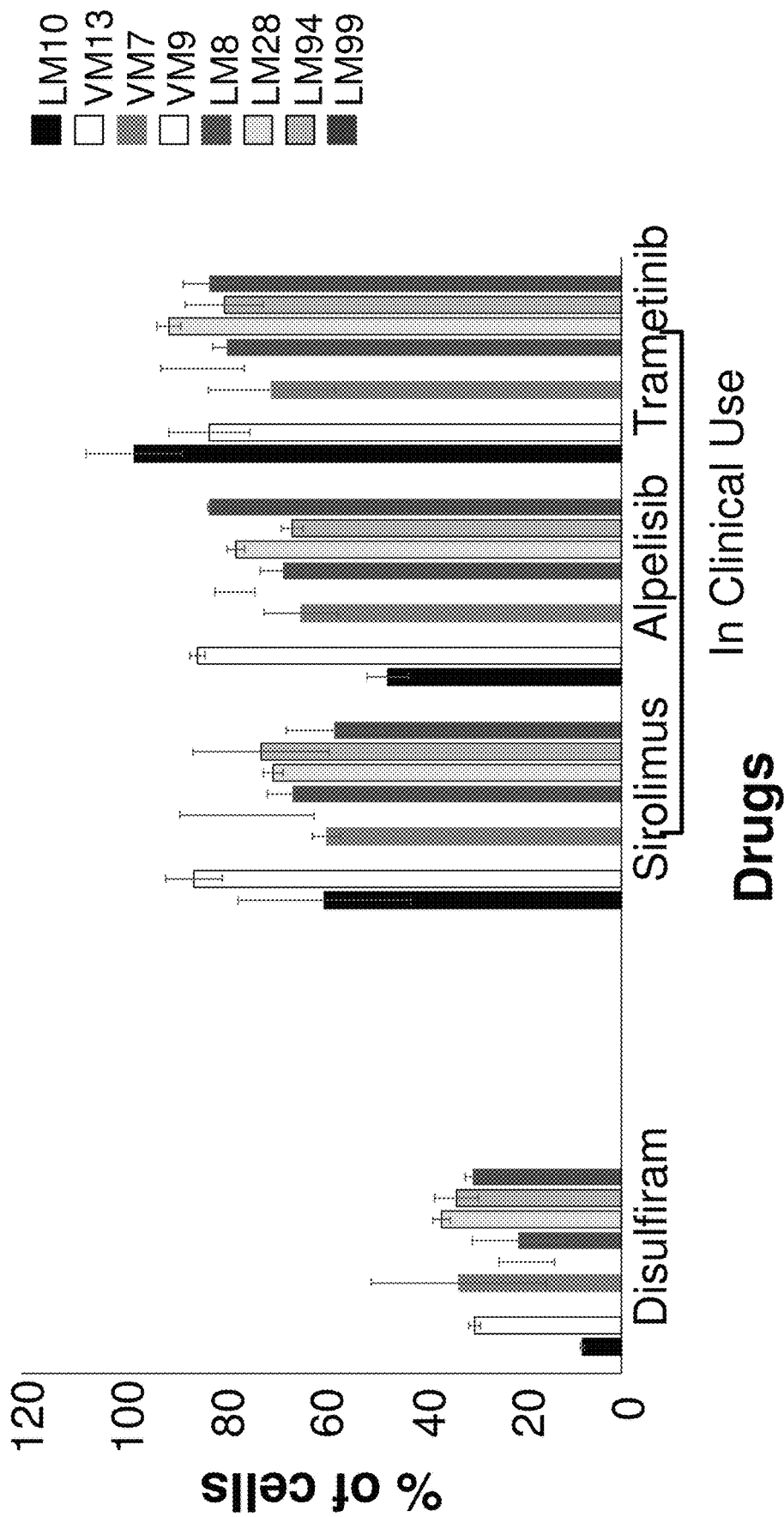
FIG. 9—Disulfiram efficaciously suppressed VMEC and LMEC growth/viability more than that observed for drugs used off label for vascular malformation patients. Using HTPS, cells were treated with 1 μM of compounds. Cell viability relative to vehicle treated cells was determined after 48 hours. Data presented for disulfiram against sirolimus, alpelisib, and trametinib, all of which have been used off label for vascular malformation patients.

Example 6—Unbiased High Throughput Screening (HTS) of ECs Additionally Identified Disulfiram as Effective Using the HTPS described in Example 2, disulfiram was also shown to efficaciously suppress VMEC and LMEC growth/viability more than that observed for drugs used off label for vascular malformation patients. See FIG. 9 and Table 4.

As can be seen in Table 4, the disulfiram tested in the HTPS ranged from number 3 to number 19 for effectiveness in the variants tested. In contrast, sirolimus and alpelisib ranged from number 28-383 for effectiveness for all variants.

REFERENCES

Basler et al., Co-inhibition of immunoproteasome subunits LMP2 and LMP7 is required to block autoimmunity. *EMBO Rep.*, 2018. 19(12):e46512.

Behravesh et al., Venous malformations: clinical diagnosis and treatment. *Cardiovasc Diagn Ther*, 2016. 6(6): 557-569.

Brown et al., Pharmacokinetics of carfilzomib in patients with advanced malignancies and varying degrees of hepatic impairment: an open-label, single-arm, phase 1 study. *Exp hematol Oncol*, 2017. 6: 27.

Chen et al., Disulfiram, a clinically used anti-alcoholism drug and copper-binding agent, induces apoptotic cell death in breast cancer cultures and xenografts via inhibition of the proteasome activity. *Cancer Res.* 2006. 66(21): 10425-33.

Chen and Dou, New uses for old copper-binding drugs: converting the pro-angiogenic copper to a specific cancer cell death inducer. *Expert Opin. Ther. Targets* 2008. 12(6): 739-48.

Dompmartin et al., Association of localized intravascular coagulopathy with venous malformations. *Arch Dermatol*, 2008. 144(7): 873-7.

Foster et al., Kaposiform lymphangiomatosis effectively treated with MEK inhibition. *EMBO Mol Med*, 2020. 12(10): e12324.

Gallerani et al., A first in human phase I study of the proteasome inhibitor CEP-18770 in patients with advanced solid tumours and multiple myeloma. *Eur J Cancer* 2013, 49: 290-296.

Greene and Vascular Anomalies: From a Clinicohistologic to a Genetic Framework. *Plast Reconstr Surg*, 2018. 141(5): 709e-717e.

Gupta et al., Pharmacokinetics of ixazomib, an oral proteasome inhibitor, in solid tumour patients with moderate or severe hepatic impairment. *Br J Pharmacol* 2016. 82: 728-38.

Hammill et al., Sirolimus for the treatment of complicated vascular anomalies in children. *Pediatr Blood Cancer*, 2011. 57(6): 1018-24.

Hari et al., Efficacy and safety results from a phase 1b/2, multicenter, open-label study of oprozomib and dexamethasone in patients with relapsed and/or refractory multiple myeloma. *Leukemia Res* 2019. 83: 106172.

Harrison et al., Phase I Clinical Trial of Marizomib (NPI-0052) in Patients with Advanced Malignancies Including Multiple Myeloma: Study NPI-0052-102 Final Results. *Clin Cancer Res* 2016. 22: 4559-66.

Infante et al., A first-in-human dose-escalation study of the oral proteasome inhibitor oprozomib in patients with advanced solid tumors. *Invest New Drugs* 2016, 34: 216-224.

Lopez Gutierrez et al., Alpelisib Treatment for Genital Vascular Malformation in a Patient with Congenital Lipomatous Overgrowth, Vascular Malformations, Epidermal Nevi, and Spinal/Skeletal Anomalies and/or Scoliosis (CLOVES) Syndrome. *J Pediatr Adolesc Gynecol*, 2019. 32(6): 648-650.

Lukey et al., A randomized, placebo-controlled study of omipalisib (PI3K/mTOR) in idiopathic pulmonary fibrosis. *European Resp. Jour.*, 2019. 53: 1801992.

Mazereeuw-Hautier et al., Extensive venous/lymphatic malformations causing life-threatening haematological complications. *Br J Dermatol*, 2007. 157(3): 558-63.

Nikolaev et al., Somatic Activating KRAS Mutations in Arteriovenous Malformations of the Brain. *N Engl J Med*, 2018. 378(3): 250-261.

Ou et al., Physiologically-based pharmacokinetic modelling to predict oprozomib CYP3A drug-drug interaction potential in patients with advanced malignancies. *Br J Pharmacol* 2019. 85: 530-539.

Potente and Makinen, Vascular heterogeneity and specialization in development and disease. *Nat Rev Mol Cell Biol*, 2017. 18(8): 477-494.

Teicher and Tomaszewski, Proteasome inhibitors. *Biochem Pharmacol*, 2015. 96(1): 1-9.

Shabaneh et al. Molecular Basis of Differential Sensitivity of Myeloma Cells to Clinically Relevant Bolus Treatment with Bortezomib. *PLOS One.*, 2013.

Uller, et al., Arteriovenous malformations. *Semin Pediatr Surg*, 2014. 23(4): 203-7.

The invention claimed is:

1. A method of treating a vascular malformation in a subject in need thereof, the method comprising administering to the subject a therapeutically effective amount of disulfiram, wherein the vascular malformation is chosen from the group consisting of lymphatic, venous, capillary, and combinations thereof.

2. The method of claim 1, wherein the disulfiram is administered to the subject by oral administration, parental administration, topical administration, or injection.

3. The method of claim 1, wherein the subject is under 10 years old.

4. The method of claim 1, wherein the subject is under 5 years old.

5. The method of claim 1, wherein the subject is under 1 year old.

6. The method of claim 1, further comprising, prior to administration, obtaining endothelial cells from the vascular malformation of the subject and testing the efficacy and/or dosage of the disulfiram on endothelial cells obtained from the subject.

* * * * *